US011241441B2

(12) United States Patent
Pellegrini

(10) Patent No.: US 11,241,441 B2
(45) Date of Patent: Feb. 8, 2022

(54) FORMULATIONS OF LIXIVAPTAN FOR THE TREATMENT OF POLYCYSTIC DISEASE

(71) Applicant: PALLADIO BIOSCIENCES, INC., Newtown, PA (US)

(72) Inventor: Lorenzo Pellegrini, Newtown, PA (US)

(73) Assignee: PALLADIO BIOSCIENCES, INC., Newtown, PA (US)

( * ) Notice: Subject to any disclaimer, the term of this patent is extended or adjusted under 35 U.S.C. 154(b) by 0 days.

(21) Appl. No.: 16/620,144

(22) PCT Filed: Jun. 8, 2018

(86) PCT No.: PCT/US2018/036719
§ 371 (c)(1),
(2) Date: Dec. 6, 2019

(87) PCT Pub. No.: WO2018/227128
PCT Pub. Date: Dec. 13, 2018

(65) Prior Publication Data
US 2020/0147102 A1 May 14, 2020

Related U.S. Application Data

(60) Provisional application No. 62/580,167, filed on Nov. 1, 2017, provisional application No. 62/517,793, filed on Jun. 9, 2017.

(51) Int. Cl.
*A61K 31/55* (2006.01)
*A61K 31/5517* (2006.01)
*A61P 13/12* (2006.01)

(52) U.S. Cl.
CPC .......... *A61K 31/5517* (2013.01); *A61P 13/12* (2018.01)

(58) Field of Classification Search
CPC .......................... A61K 31/5517; A61P 13/12
USPC ........................................................ 514/220
See application file for complete search history.

(56) References Cited

U.S. PATENT DOCUMENTS

| 5,516,774 A * | 5/1996 | Albright ................... A61P 7/00 514/220 |
| 5,972,882 A | 10/1999 | Gattone, II |
| 6,352,718 B1 * | 3/2002 | Yoon .................... A61K 9/4866 424/456 |
| 2008/0221084 A1 | 9/2008 | Liu et al. |
| 2013/0079334 A1 | 3/2013 | Chen et al. |
| 2015/0283147 A1 | 10/2015 | Proia et al. |

FOREIGN PATENT DOCUMENTS

WO WO-2016077370 A1 * 5/2016 ........... A61K 31/551

OTHER PUBLICATIONS

International Search Report for International Application No. PCT/US2018/036719 dated Aug. 30, 2018, 3 pages.
Written Opinion for International Application No. PCT/US2018/036719 dated Aug. 30, 2018, 5 pages.
(Continued)

*Primary Examiner* — Shengjun Wang
(74) *Attorney, Agent, or Firm* — Morgan, Lewis & Bockius LLP

(57) ABSTRACT

Formulations of lixivaptan, and methods of using the same, are provided for the treatment of polycystic disease.

19 Claims, 6 Drawing Sheets

Exemplary Divided Doses of Lixivaptan

(56) References Cited

OTHER PUBLICATIONS

Extended European Search Report dated Feb. 10, 2021 for European Patent Application No. 18814459.6.
J. Pharmacokinet. Pharmacodyn. 2017, 44, S70 (T-036).
J. Am. Soc. Nephrol. 2017, 28(10 Suppl. 1 ), 485—Abstract FR-P0326.
J. Am. Soc. Nephrol. 2018, 29(10 Suppl. 1 ), 870—Abstract SA-P0516.

* cited by examiner

A = normal renal function; E = end-stage renal disease

Exemplary Divided Doses of Lixivaptan

| 800 mg daily dose | | 700 mg daily dose | | 600 mg daily dose | | 500 mg daily dose | | 400 mg daily dose | | 300 mg daily dose | | 200 mg daily dose | |
|---|---|---|---|---|---|---|---|---|---|---|---|---|---|
| Dose 1 | Dose 2 | Dose 1 | Dose 2 | Dose 1 | Dose 2 | Dose 1 | Dose 2 | Dose 1 | Dose 2 | Dose 1 | Dose 2 | Dose 1 | Dose 2 |
| 775 | 25 | 675 | 25 | 575 | 25 | 475 | 25 | 375 | 25 | 275 | 25 | 175 | 25 |
| 750 | 50 | 650 | 50 | 550 | 50 | 450 | 50 | 350 | 50 | 250 | 50 | 150 | 50 |
| 725 | 75 | 625 | 75 | 525 | 75 | 425 | 75 | 325 | 75 | 225 | 75 | 125 | 75 |
| 700 | 100 | 600 | 100 | 500 | 100 | 400 | 100 | 300 | 100 | 200 | 100 | 100 | 100 |
| 675 | 125 | 575 | 125 | 475 | 125 | 375 | 125 | 275 | 125 | 175 | 125 | 75 | 125 |
| 650 | 150 | 550 | 150 | 450 | 150 | 350 | 150 | 250 | 150 | 150 | 150 | 50 | 150 |
| 625 | 175 | 525 | 175 | 425 | 175 | 325 | 175 | 225 | 175 | 125 | 175 | 25 | 175 |
| 600 | 200 | 500 | 200 | 400 | 200 | 300 | 200 | 200 | 200 | 100 | 200 | | |
| 575 | 225 | 475 | 225 | 375 | 225 | 275 | 225 | 175 | 225 | 75 | 225 | | |
| 550 | 250 | 450 | 250 | 350 | 250 | 250 | 250 | 150 | 250 | 50 | 250 | | |
| 525 | 275 | 425 | 275 | 325 | 275 | 225 | 275 | 125 | 275 | 25 | 275 | | |
| 500 | 300 | 400 | 300 | 300 | 300 | 200 | 300 | 100 | 300 | | | | |
| 475 | 325 | 375 | 325 | 275 | 325 | 175 | 325 | 75 | 325 | | | | |
| 450 | 350 | 350 | 350 | 250 | 350 | 150 | 350 | 50 | 350 | | | | |
| 425 | 375 | 325 | 375 | 225 | 375 | 125 | 375 | 25 | 375 | | | | |
| 400 | 400 | 300 | 400 | 200 | 400 | 100 | 400 | | | | | | |
| 375 | 425 | 275 | 425 | 175 | 425 | 75 | 425 | | | | | | |
| 350 | 450 | 250 | 450 | 150 | 450 | 50 | 450 | | | | | | |
| 325 | 475 | 225 | 475 | 125 | 475 | 25 | 475 | | | | | | |
| 300 | 500 | 200 | 500 | 100 | 500 | | | | | | | | |
| 275 | 525 | 175 | 525 | 75 | 525 | | | | | | | | |
| 250 | 550 | 150 | 550 | 50 | 550 | | | | | | | | |
| 225 | 575 | 125 | 575 | 25 | 575 | | | | | | | | |
| 200 | 600 | 100 | 600 | | | | | | | | | | |
| 175 | 625 | 75 | 625 | | | | | | | | | | |
| 150 | 650 | 50 | 650 | | | | | | | | | | |
| 125 | 675 | 25 | 675 | | | | | | | | | | |
| 100 | 700 | | | | | | | | | | | | |
| 75 | 725 | | | | | | | | | | | | |
| 50 | 750 | | | | | | | | | | | | |
| 25 | 775 | | | | | | | | | | | | |

FIG. 6

FORMULATIONS OF LIXIVAPTAN FOR THE TREATMENT OF POLYCYSTIC DISEASE

CROSS-REFERENCE TO RELATED APPLICATIONS

This application is a U.S. National Stage application of International Patent Application No. PCT/US2018/036719 filed Jun. 8, 2018, which claims the benefit of U.S. Provisional Patent Application Nos. 62/517,793 filed Jun. 9, 2017, and 62/580,167 filed Nov. 1, 2017, all of which are incorporated by reference herein in their entireties.

FIELD OF THE INVENTION

The invention relates generally to formulations of lixivaptan and methods of using the same for the treatment of polycystic diseases and more particularly, but not exclusively, to divided dose formulations of lixivaptan and methods of using the same for the treatment of polycystic kidney diseases, such as autosomal dominant polycystic kidney disease.

BACKGROUND OF THE INVENTION

Polycystic kidney disease is the most common inherited kidney disease and a leading cause of end-stage kidney disease in adults worldwide (Grantham N Engl J Med 2008; 359:1477-85). There are two recognized forms, autosomal dominant polycystic kidney disease (ADPKD) and autosomal recessive polycystic kidney disease (ARPKD). Most cases of ADPKD are due to mutations in the PKD1 gene, with a minority of cases due to mutations in PKD2. PKD1 and PKD2 encode for polycystin-1 and polycystin-2 proteins (polycystin signaling complex) which regulate different signals including 3',5'-cyclic adenosine monophosphate (cAMP), mammalian target of rapamycin (mTOR) and epidermal growth factor receptor pathways. Further, it has been shown that GANAB (encoding glucosidase II subunit α) mutations are responsible for some previously genetically unresolved cases of ADPKD, likely driven by defects in PC1 maturation (Porath et al 2016 Am J Hum Genet 98(6):1193-207).

ADPKD is a late-onset progressive disease, typically but not always asymptomatic until adulthood, when the development of renal cysts can be observed, followed by their expansion which leads ultimately to kidney failure. The complications of ADPKD develop on the basis of the number, size, and location of cysts. A large total kidney volume has been associated with hypertension, gross hematuria, nephrolithiasis, and pain in many studies. Cysts can also occur in other organs such as the liver, pancreas, arachnoid membrane and seminal vesicles. ARPKD is a substantial cause of morbidity and mortality in children and is caused by mutations in the PKHD1 gene, encoding fibrocystin (FPC), and both the gene and protein interact with the autosomal dominant polycystic kidney disease (ADPKD) genes and proteins.

Studies of animal models implicate the antidiuretic hormone arginine vasopressin and its second messenger adenosine-3',5'-cyclic monophosphate (cAMP) as promoters of kidney-cyst cell proliferation and luminal fluid secretion. In these models, the suppression of vasopressin release by means of high water intake, genetic elimination of vasopressin, and vasopressin V2-receptor blockade all reduce the cyst burden and protect kidney function (Wang, X. et al., 2005 J Am Soc Nephrol 16: 846-851). Such preclinical studies led to clinical trials on the effects of tolvaptan, a vasopressin V2-receptor antagonist, in human ADPKD. However, the potential benefits of tolvaptan are significantly impacted by its associated risk factors and side effects. Thirst, polyuria, and related adverse events may affect the ability of some patients to take effective doses of tolvaptan. Furthermore, the elevation of alanine aminotransferase enzyme concentrations (a liver enzyme) indicated the potential for acute liver failure (Tones, V E. et al., 2012 NEJM 367:2407-18).

Effective treatment for PKD remains lacking. Accordingly, there is a need in the field for improved methods of treating PKD with reduced side effects or adverse events.

SUMMARY OF THE INVENTION

In order to address the needs in the field, the invention includes lixivaptan formulations and methods of using the same in the treatment of polycystic disease. In some embodiments, the polycystic disease is polycystic kidney disease (PKD) or polycystic liver disease.

In an embodiment, the invention includes a method of treating polycystic disease in a human subject. In some embodiments, the methods include administering to the subject a therapeutically effective amount of a pharmaceutical composition comprising lixivaptan or a pharmaceutically acceptable salt, prodrug, solvate, tautomer, or hydrate thereof, and a pharmaceutically acceptable carrier, wherein the composition comprises 200 mg to 800 mg lixivaptan.

In an embodiment, the invention includes a pharmaceutical composition for treating a polycystic disease in a human subject in need thereof. In some embodiments, the pharmaceutical composition includes a therapeutically effective amount of lixivaptan, or a pharmaceutically acceptable salt thereof, and a pharmaceutically acceptable carrier, wherein the therapeutically effective amount is about 200 mg to about 800 mg lixivaptan.

BRIEF DESCRIPTION OF THE DRAWINGS

The foregoing summary, as well as the following detailed description of the invention, will be better understood when read in conjunction with the appended drawings.

FIG. 6 provides a table illustrating exemplary embodiments of lixivaptan dosages when used in a divided-dose or split-dose treatment strategy for 200 mg, 300 mg, 400 mg, 500 mg, 600 mg, 700 mg, or 800 mg daily doses.

DETAILED DESCRIPTION OF THE INVENTION

Figure 1:
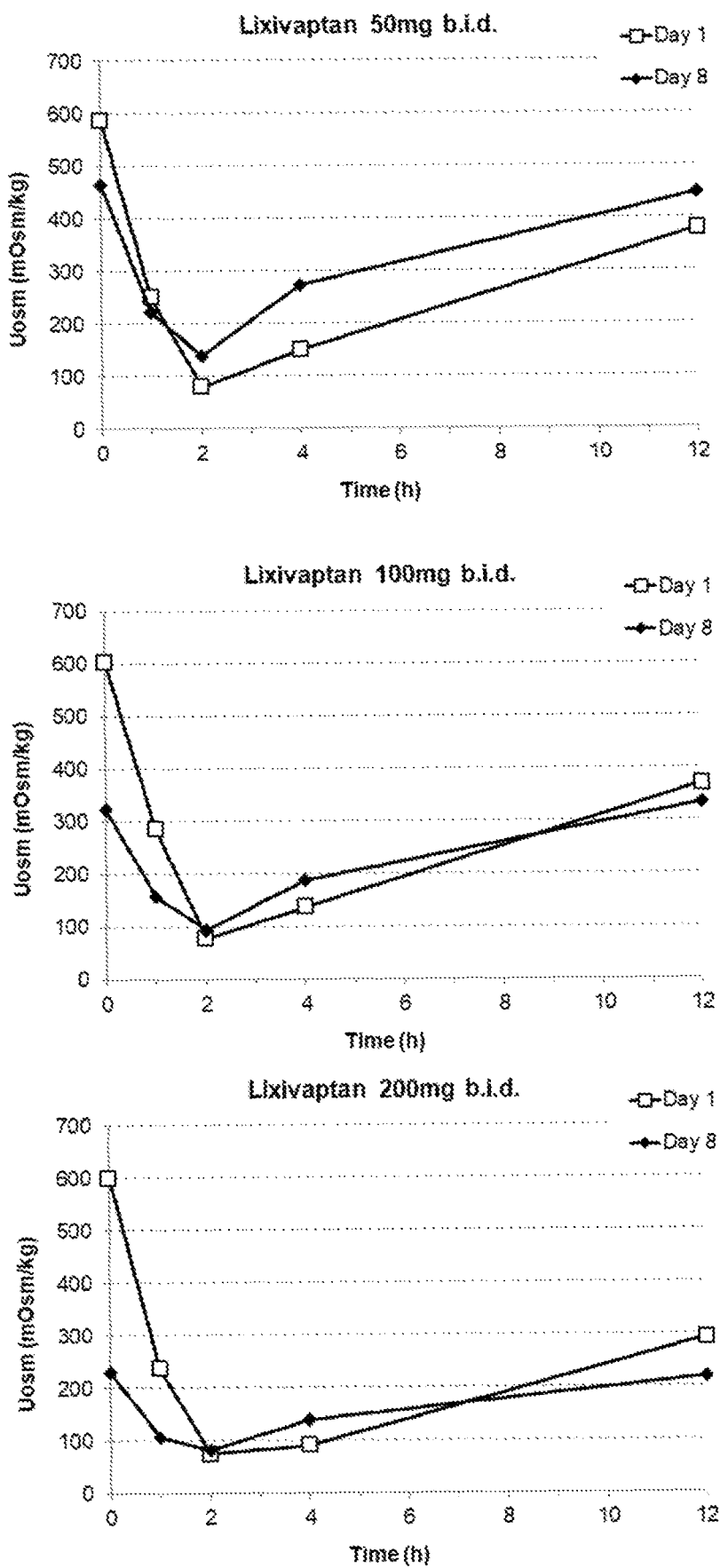
FIG. 1 illustrates the time course of mean $U_{osm}$ on day 1 and Day 8 following twice daily oral doses of lixivaptan in healthy volunteers.
Figure 2:
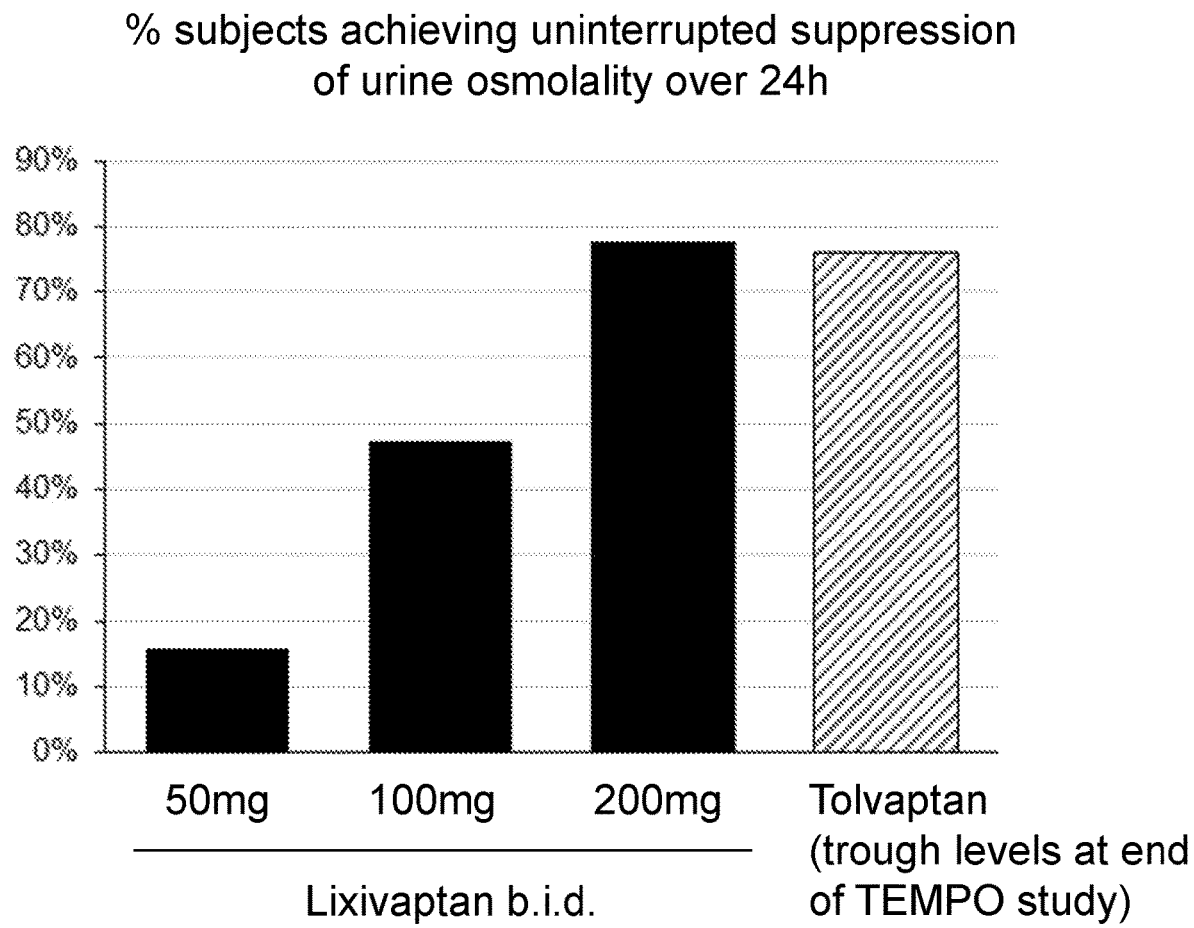
FIG. 2 illustrates patients treated with lixivaptan compared to tolvaptan where the y-axis is the % of subjects achieving uninterrupted urine osmolality suppression below target level during 24 hours.

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" refer to lixivaptan or a pharmaceutically acceptable salt, prodrug, hydrate, cocrystal, conformer, polymorph, crystalline form, tautomer, or solvate thereof.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The phrases "therapeutically effective amount" and "therapeutically effective dose" in general, unless otherwise specified, refers to an amount of lixivaptan that, when administered to a subject for treating polycystic disease, is sufficient to effect treatment of polycystic disease (e.g., polycystic kidney disease or polycystic liver disease). More specifically, a therapeutically effective amount or dose refers to an amount of lixivaptan that, when administered according to a recited regimen, is effective to prevent, alleviate or ameliorate symptoms or signs of polycystic disease or prolong the survival of the subject being treated. The "therapeutically effective amount" or "dose" may vary somewhat depending on the severity of renal compromise. "Therapeutic ratio" as used herein refers to a comparison of the therapeutic effect to the toxicity or adverse effect of lixivaptan. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the dosing regimen to be followed, whether the compound is administered in combination with other compounds, timing of administration, the tissue to which it is administered, and the physical delivery system in which the compound is carried.

"Divided dose" or "divided dose regimen" refers to a number of administrations of drug that are made over the course of a specified time period to reach a specified total dose. For example, a total daily dose of 300 mg can be administered in two doses, one taken by the subject in the morning and one taken by the subject in the evening before going to sleep. In some embodiments, a first dose in the morning can be 200 mg, and the second dose in the evening can be 100 mg, thus achieving the daily dose of 300 mg.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable" refers to those compounds, materials, compositions, carriers, and/or dosage forms which are, within the scope of sound medical judgment, suitable for use in contact with the tissues of human beings without excessive toxicity, irritation, allergic response, or other problem or complication, commensurate with a reasonable benefit/risk ratio.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs disclosed herein, can also be incorporated into the described compositions and methods.

As used herein, the terms "treating" or "treatment" as used herein refer to controlling, treating, or preventing the progression of polycystic disease (e.g., polycystic kidney disease or polycystic liver disease). The term "controlling", "treating" or "treatment" of polycystic disease (e.g., polycystic kidney disease or polycystic liver disease) includes, without limitation: (1) preventing polycystic disease (e.g., polycystic kidney disease or polycystic liver disease), i.e. causing the clinical symptoms or signs of the disease not to develop in a subject that is predisposed to the disease but does not yet experience or display symptoms/signs of the disease; or (2) inhibiting the disease, i.e., arresting or reducing the progression of the disease or its clinical symptoms or signs.

As used herein, the term "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid of lixivaptan so modified to include such moieties. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein include esters and carbonates formed by reacting one or more hydroxyls of lixivaptan, so modified to include such moieties, with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., lixivaptan) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Use of the term "about" when referring to the number of hours, the variation is typically from 0 to 2 minutes, 2 to 4 minutes, 4 to 6 minutes, 6 to 8 minutes, 8 to 10 minutes, 10 to 12 minutes, 12 to 15 minutes, 2 to 5 minutes, 5 to 8 minutes, 8 to 11 minutes, 11 to 15 minutes, 2 to 6 minutes, 6 to 10 minutes, 10 to 15 minutes, 2 to 7 minutes, 7 to 12 minutes, 12 to 15 minutes, 2 to 8 minutes, 8 to 15 minutes, 2 to 9 minutes, 9 to 15 minutes, 3 to 6 minutes, 6 to 9 minutes, 4 to 8 minutes, 8 to 12 minutes, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes of the stated number or numerical range.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Solvate" refers to a compound in physical association with one or more molecules of a pharmaceutically acceptable solvent.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that time, dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, time, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of."

Lixivaptan and Variants Thereof

Lixivaptan (also known as VPA-985, BIIB030, and CL 347,985; CAS Registry Number 168079-32-1) is a potent, non-peptide selective antagonist for the vasopressin V2 receptor. The chemical name of lixivaptan is 5-fluoro-2-methyl-N-[4-(5H-pyrrolo[2,1-C] [1,4]benzodiazepin-10 (11H)-yl carbonyl)-3-chlorophenyl]benzamide. Lixivaptan is generally described as a benzoazepine. An exemplary synthesis of lixivaptan has been presented in Albright, et al., J. Med. Chem. (1998) 41: 2442-2444 and the structure of lixivaptan is shown below:

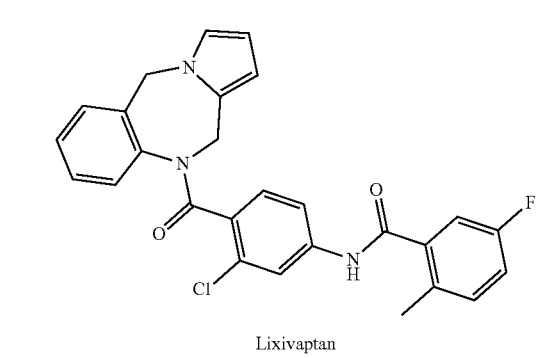 [SMILES: Cc1ccc(F)cc1C(=O)Nc1ccc(C(=O)N2Cc3cccn3Cc3ccccc32)c(Cl)c1]

Lixivaptan

Lixivaptan antagonizes the effects of vasopressin that are mediated by the V2 receptor, resulting in the pharmacologic effect of increased free water excretion, thus decreasing urine osmolality ($U_{osm}$), increasing urine flow and increasing serum osmolality ($S_{osm}$). It has been studied clinically for the treatment of hyponatremia. However, the doses studied for the effective treatment of hyponatremia did not result in inhibition of vasopressin V2 receptor activity, as measured by a reduction in $U_{osm}$ that would be useful for treating PKD. Therefore, it is an object of this invention to provide doses of lixivaptan that can treat PKD without some of the significant adverse effects that would limit or prohibit effective treatment of the disease in some subjects.

In an embodiment, lixivaptan, as described herein, encompasses lixivaptan pharmaceutically acceptable salts, prodrugs, solvates, cocrystals, conformer, polymorph, crystalline form, tautomers, or hydrates thereof.

Methods of Treating Polycystic Disease with Lixivaptan

In an embodiment, the invention includes methods of treating polycystic disease in a human subject in need of such treatment. In some embodiments, the invention includes methods of treating polycystic kidney disease (PKD) or polycystic liver disease. In some embodiments, the polycystic kidney disease (PKD) treated by the methods of the invention may be autosomal dominant polycystic kidney disease (ADPKD).

In some embodiments, the methods of the invention include administering a therapeutically effective amount of lixivaptan, or a pharmaceutically acceptable salt, prodrug, solvate, cocrystal, conformer, polymorph, crystalline form, tautomer, or hydrate thereof, to the human subject.

In some embodiments, the methods of the invention include administering a therapeutically effective amount of a pharmaceutical composition comprising lixivaptan, or a pharmaceutically acceptable salt, prodrug, solvate, cocrystal, conformer, polymorph, crystalline form, tautomer, or hydrate thereof, and a pharmaceutically acceptable carrier, to the human subject.

In some embodiments, the methods of the invention include the step of administering a first pharmaceutical composition to the human subject, comprising lixivaptan, or a pharmaceutically acceptable salt, prodrug, solvate, cocrystal, conformer, polymorph, crystalline form, tautomer, or hydrate thereof, and a pharmaceutically acceptable carrier, at a first dose, as described herein.

In some embodiments, the methods of the invention include the step of administering a second pharmaceutical composition to the human subject, comprising lixivaptan, or a pharmaceutically acceptable salt, prodrug, solvate, cocrystal, conformer, polymorph, crystalline form, tautomer, or hydrate thereof, and a pharmaceutically acceptable carrier, at a second dose, as described herein, wherein the second pharmaceutical composition is delivered to the human subject after a first period.

In an embodiment, the first pharmaceutical composition and the second pharmaceutical composition are the same.

In some embodiments, the first period is about 1 hour to about 24 hours, or about 2 hours to about 23 hours, or about 3 hours to about 22 hours, or about 4 hours to about 21 hours, or about 5 hours to about 20 hours, or about 6 hours to about 19 hours, or about 7 hours to about 18 hours, or about 8 hours to about 9 hours, or about 8 hours to about 10 hours, or about 8 hours to about 11 hours, or about 8 hours to about 12 hours, or about 8 hours to about 13 hours, or about 8 hours to about 14 hours, or about 8 hours to about 15 hours, or about 8 hours to about 16 hours, or about 8 hours to about 17 hours, about 9 hours to about 10 hours, or about 9 hours to about 11 hours, or about 9 hours to about 12 hours, or about 9 hours to about 13 hours, or about 9 hours to about 14 hours, or about 9 hours to about 15 hours, or about 9 hours to about 16 hours, or about 9 hours to about 17 hours, about 10 hours to about 11 hours, or about 10 hours to about 12 hours, or about 10 hours to about 13 hours, or about 10 hours to about 14 hours, or about 10 hours to about 15 hours, or about 10 hours to about 16 hours, or about 10 hours to about 17 hours, or about 11 hours to about 12 hours, or about 11 hours to about 13 hours, or about 11 hours to about 14 hours, or about 11 hours to about 15 hours, or about 11 hours to about 16 hours, or about 11 hours to about 17 hours or at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at most 1 hour, or at most 2 hours, or at most 3 hours, or at most 4 hours, or at most 5 hours, or at most 6 hours, or at most 7 hours, or at most 8 hours, or at most 9 hours, or at most 10 hours, or at most 11 hours, or at most 12 hours, or at most 13 hours, or at most 14 hours, or at most 15 hours, or at most 16 hours, or at most 17 hours, or at most 18 hours, or at most 19 hours, or at most 20 hours, or at most 21 hours, or at most 22 hours, or at most 23 hours, or about 1 hour, or about 2 hours, or about 3 hours, or about 4 hours, or about 5 hours, or about 6 hours, or about 7 hours, or about 8 hours, or about 9 hours, or about 10 hours, or about 11 hours, or about 12 hours, or about 13 hours, or about 14 hours, or about 15 hours, or about 16 hours, or about 17 hours, or about 18 hours, or about 19 hours, or about 20 hours or about 21 hours, or about 22 hours, or about 23 hours, or about 24 hours.

In some embodiments, the methods of the invention include the step of administering a third pharmaceutical composition to the human subject, comprising lixivaptan, or a pharmaceutically acceptable salt, prodrug, solvate, cocrystal, conformer, polymorph, crystalline form, tautomer, or hydrate thereof, and a pharmaceutically acceptable carrier, at a third dose, as described herein, wherein the third pharmaceutical composition is delivered to the human subject after a second period.

In some embodiments, the second period is about 1 hour to about 24 hours, or about 2 hours to about 23 hours, or about 3 hours to about 22 hours, or about 4 hours to about 21 hours, or about 5 hours to about 20 hours, or about 6 hours to about 19 hours, or about 7 hours to about 18 hours, or about 8 hours to about 9 hours, or about 8 hours to about 10 hours, or about 8 hours to about 11 hours, or about 8 hours to about 12 hours, or about 8 hours to about 13 hours, or about 8 hours to about 14 hours, or about 8 hours to about 15 hours, or about 8 hours to about 16 hours, or about 8 hours to about 17 hours, about 9 hours to about 10 hours, or about 9 hours to about 11 hours, or about 9 hours to about 12 hours, or about 9 hours to about 13 hours, or about 9 hours to about 14 hours, or about 9 hours to about 15 hours, or about 9 hours to about 16 hours, or about 9 hours to about 17 hours, about 10 hours to about 11 hours, or about 10 hours to about 12 hours, or about 10 hours to about 13 hours, or about 10 hours to about 14 hours, or about 10 hours to about 15 hours, or about 10 hours to about 16 hours, or about 10 hours to about 17 hours, or about 11 hours to about 12 hours, or about 11 hours to about 13 hours, or about 11 hours to about 14 hours, or about 11 hours to about 15 hours, or about 11 hours to about 16 hours, or about 11 hours to about 17 hours or at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at most 1 hour, or at most 2 hours, or at most 3 hours, or at most 4 hours, or at most 5 hours, or at most 6 hours, or at most 7 hours, or at most 8 hours, or at most 9 hours, or at most 10 hours, or at most 11 hours, or at most 12 hours, or at most 13 hours, or at most 14 hours, or at most 15 hours, or at most 16 hours, or at most 17 hours, or at most 18 hours, or at most 19 hours, or at most 20 hours, or at most 21 hours, or at most 22 hours, or at most 23 hours, or about 1 hour, or about 2 hours, or about 3 hours, or about 4 hours, or about 5 hours, or about 6 hours, or about 7 hours, or about 8 hours, or about 9 hours, or about 10 hours, or about 11 hours, or about 12 hours, or about 13 hours, or about 14 hours, or about 15 hours, or about 16 hours, or about 17 hours, or about 18 hours, or about 19 hours, or about 20 hours or about 21 hours, or about 22 hours, or about 23 hours, or about 24 hours.

In some embodiments, the first dose, second dose, and/or third dose, if applicable, in a 24 hour period are the same amount.

In some embodiments, the first dosage is greater than the second dose. In some embodiments, the first dose is greater than the third dose.

In some embodiments, the second dose is greater than the first dose. In some embodiments, the second dose is greater than the third dose.

In some embodiments, the third dose is greater than the first dose. In some embodiments, the third dose is greater than the second dose.

In some embodiments, the first dose is about 5 mg to about 1000 mg, or about 5 mg to about 25 mg, or about 25 mg to about 50 mg, or about 50 mg to about 75 mg, or about 75 mg to about 100 mg, or about 100 mg to about 125 mg, or about 125 mg to about 150 mg, or about 150 mg to about 175 mg, or about 175 mg to about 200 mg, or about 200 mg to about 225 mg, or about 225 mg to about 250 mg, or about 250 mg to about 275 mg, or about 275 mg to about 300 mg, or about 300 mg to about 325 mg, or about 325 mg to about 350 mg, or about 350 mg to about 375 mg, or about 375 mg to about 400 mg, or about 400 mg to about 425 mg, or about 425 mg to about 450 mg, or about 450 mg to about 475 mg, or about 475 mg to about 500 mg, or about 500 mg to about 525 mg, or about 525 mg to about 550 mg, or about 550 mg to about 575 mg, or about 575 mg to about 600 mg, or about 600 mg to about 625 mg, or about 625 mg to about 650 mg, or about 650 mg to about 675 mg, or about 675 mg to about 700 mg, or about 700 mg to about 725 mg, or about 725 mg to about 750 mg, or about 750 mg to about 775 mg, or about 775 mg to about 800 mg, or at least 5 mg, or at least 25 mg, or at least 50 mg, or at least 75 mg, or at least 100 mg, or at least 125 mg, or at least 150 mg, or at least 175 mg, or at least 200 mg, or at least 225 mg, or at least 250 mg, or at least 275 mg, or at least 300 mg, or at least 325 mg, or at least 350 mg, or at least 375 mg, or at least 400 mg, or at least 425 mg, or at least 450 mg, or at least 475 mg, or at least 500 mg, or at least 525 mg, or at least 550 mg, or at least 575 mg, or at least 600 mg, or at least 625 mg, or at least 650 mg, or at least 650 mg, or at least 675 mg, or at least 700 mg, or at least 725 mg, or at least 750 mg, or at least 775 mg, or at least 800 mg, or at most 5 mg, or at most 25 mg, or at most 50 mg, or at most 75 mg, or at most 100 mg, or at most 125 mg, or at most 150 mg, or at most 175 mg, or at most 200 mg, or at most 225 mg, or at most 250 mg, or at most 275 mg, or at most 300 mg, or at most 325 mg, or at most 350 mg, or at most 375 mg, or at most 400 mg, or at most 425 mg, or at most 450 mg, or at most 475 mg, or at most 500 mg, or at most 525 mg, or at most 550 mg, or at most 575 mg, or at most 600 mg, or at most 625 mg, or at most 650 mg, or at most 650 mg, or at most 675 mg, or at most 700 mg, or at most 725 mg, or at most 750 mg, or at most 775 mg, or at most 800 mg, or about 5 mg, or about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 650 mg, or about 675 mg, or about 700 mg, or about 725 mg, or about 750 mg, or about 775 mg, or about 800 mg.

In some embodiments, the second dose is about 5 mg to about 1000 mg, or about 5 mg to about 25 mg, or about 25 mg to about 50 mg, or about 50 mg to about 75 mg, or about 75 mg to about 100 mg, or about 100 mg to about 125 mg, or about 125 mg to about 150 mg, or about 150 mg to about 175 mg, or about 175 mg to about 200 mg, or about 200 mg to about 225 mg, or about 225 mg to about 250 mg, or about 250 mg to about 275 mg, or about 275 mg to about 300 mg, or about 300 mg to about 325 mg, or about 325 mg to about 350 mg, or about 350 mg to about 375 mg, or about 375 mg to about 400 mg, or about 400 mg to about 425 mg, or about 425 mg to about 450 mg, or about 450 mg to about 475 mg, or about 475 mg to about 500 mg, or about 500 mg to about 525 mg, or about 525 mg to about 550 mg, or about 550 mg to about 575 mg, or about 575 mg to about 600 mg, or about 600 mg to about 625 mg, or about 625 mg to about 650 mg, or about 650 mg to about 675 mg, or about 675 mg to about 700 mg, or about 700 mg to about 725 mg, or about 725 mg to about 750 mg, or about 750 mg to about 775 mg, or about 775 mg to about 800 mg, or at least 5 mg, or at least 25 mg, or at least 50 mg, or at least 75 mg, or at least 100 mg, or at least 125 mg, or at least 150 mg, or at least 175 mg, or at least 200 mg, or at least 225 mg, or at least 250 mg, or at least 275 mg, or at least 300 mg, or at least 325 mg, or at least 350 mg, or at least 375 mg, or at least 400 mg, or at least 425 mg, or at least 450 mg, or at least 475 mg, or at least 500 mg, or at least 525 mg, or at least 550 mg, or at least 575 mg, or at least 600 mg, or at least 625 mg, or at least 650 mg, or at least 650 mg, or at least 675 mg, or at least 700 mg, or at least 725 mg, or at least 750 mg, or at least 775 mg, or at least 800 mg, or at most 5 mg, or at most 25 mg, or at most 50 mg, or at most 75 mg, or at most 100 mg, or at most 125 mg, or at most 150 mg, or at most 175 mg, or at most 200 mg, or at most 225 mg, or at most 250 mg, or at most 275 mg, or at most 300 mg, or at most 325 mg, or at most 350 mg, or at most 375 mg, or at most 400 mg, or at most 425 mg, or at most 450 mg, or at most 475 mg, or at most 500 mg, or at most 525 mg, or at most 550 mg, or at most 575 mg, or at most 600 mg, or at most 625 mg, or at most 650 mg, or at most 650 mg, or at most 675 mg, or at most 700 mg, or at most 725 mg, or at most 750 mg, or at most 775 mg, or at most 800 mg, or about 5 mg, or about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 650 mg, or about 675 mg, or about 700 mg, or about 725 mg, or about 750 mg, or about 775 mg, or about 800 mg.

In some embodiments, the third dose is about 5 mg to about 1000 mg, or about 5 mg to about 25 mg, or about 25 mg to about 50 mg, or about 50 mg to about 75 mg, or about 75 mg to about 100 mg, or about 100 mg to about 125 mg, or about 125 mg to about 150 mg, or about 150 mg to about 175 mg, or about 175 mg to about 200 mg, or about 200 mg to about 225 mg, or about 225 mg to about 250 mg, or about 250 mg to about 275 mg, or about 275 mg to about 300 mg, or about 300 mg to about 325 mg, or about 325 mg to about 350 mg, or about 350 mg to about 375 mg, or about 375 mg to about 400 mg, or about 400 mg to about 425 mg, or about 425 mg to about 450 mg, or about 450 mg to about 475 mg, or about 475 mg to about 500 mg, or about 500 mg to about 525 mg, or about 525 mg to about 550 mg, or about 550 mg to about 575 mg, or about 575 mg to about 600 mg, or about 600 mg to about 625 mg, or about 625 mg to about 650 mg, or about 650 mg to about 675 mg, or about 675 mg to about 700 mg, or about 700 mg to about 725 mg, or about 725 mg to about 750 mg, or about 750 mg to about 775 mg, or about 775 mg to about 800 mg, or at least 5 mg, or at least 25 mg, or at least 50 mg, or at least 75 mg, or at least 100 mg, or at least 125 mg, or at least 150 mg, or at least 175 mg, or at least 200 mg, or at least 225 mg, or at least 250 mg, or at least 275 mg, or at least 300 mg, or at least 325 mg, or at least 350 mg, or at least 375 mg, or at least 400 mg, or at least 425 mg, or at least 450 mg, or at least 475 mg, or at least 500 mg, or at least 525 mg, or at least 550 mg, or at least 575 mg, or at least 600 mg, or at least 625 mg, or at least 650 mg, or at least 650 mg, or at least 675 mg, or at least 700 mg, or at least 725 mg, or at least 750 mg, or at least 775 mg, or at least 800 mg, or at most 5 mg, or at most 25 mg, or at most 50 mg, or at most 75 mg, or at most 100 mg, or at most 125 mg, or at most 150 mg, or at most 175 mg, or at most 200 mg, or at most 225 mg, or at most 250 mg, or at most 275 mg, or at most 300 mg, or at most 325 mg, or at most 350 mg, or at most 375 mg, or at most 400 mg, or at most 425 mg, or at most 450 mg, or at most 475 mg, or at most 500 mg, or at most 525 mg, or at most 550 mg, or at most 575 mg, or at most 600 mg, or at most 625 mg, or at most 650 mg, or at most 650 mg, or at most 675 mg, or at most 700 mg, or at most 725 mg, or at most 750 mg, or at most 775 mg, or at most 800 mg, or about 5 mg, or about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 650 mg, or about 675 mg, or about 700 mg, or about 725 mg, or about 750 mg, or about 775 mg, or about 800 mg.

In some embodiments of the methods of the invention, the pharmaceutical compositions described herein are delivered once daily (e.g., a first composition).

In some embodiments, a therapeutically effective amount of a pharmaceutical composition is a first dose or a second dose or a third dose, as described herein.

In some embodiments of the methods of the invention, the pharmaceutical compositions are delivered as divided doses. In some embodiments of the methods of the invention, the pharmaceutical compositions are delivered twice daily (e.g., a first composition and a second composition). In some embodiments of the methods of the invention, the pharmaceutical compositions are delivered thrice daily (e.g., a first composition, a second composition, and a third composition). In some embodiments, the divided doses add up to a daily dose. In some embodiments, a therapeutically effective amount of divided doses of a pharmaceutical composition can be the sum of a first dose and a second dose, or a first dose and a second dose and a third dose. In an embodiment, lixivaptan can be delivered at a daily dose of 300 mg, with the first dose of 200 mg in the morning, and the second dose of 100 mg 8 to 12 hours later in the same day. In an embodiment, lixivaptan can be delivered at a daily dose of 300 mg, with the first dose of 200 mg in the morning, and the second dose of 100 mg about 8 hours later in the same day. In an embodiment, lixivaptan can be delivered at a daily dose of 300 mg, with the first dose of 200 mg in the morning, and the second dose of 100 mg about 9 hours later in the same day. In an embodiment, lixivaptan can be delivered at a daily dose of 300 mg, with the first dose of 200 mg in the morning, and the second dose of 100 mg about 10 hours later in the same day. In an embodiment, lixivaptan can be delivered at a daily dose of 300 mg, with the first dose of 200 mg in the morning, and the second dose of 100 mg about 11 hours later in the same day. In an embodiment, lixivaptan can be delivered at a daily dose of 300 mg, with the first dose of 200 mg in the morning, and the second dose of 100 mg about 12 hours later in the same day. Alternatively, lixivaptan can be delivered at a daily dose of 300 mg, with a first dose of 150 mg taken by the subject in the morning, a second dose of 100 mg taken by the subject approximately 6 to 8 hours later in the same day, and a third dose of 50 mg taken 6 to 8 hours later in the same day.

In some embodiments, a daily dose can be the sum of a first dose and a second dose, wherein the daily dose is about 25 mg to about 50 mg, or about 50 mg to about 75 mg, or about 75 mg to about 100 mg, or about 100 mg to about 125 mg, or about 125 mg to about 150 mg, or about 150 mg to about 175 mg, or about 175 mg to about 200 mg, or about 200 mg to about 225 mg, or about 225 mg to about 250 mg, or about 250 mg to about 275 mg, or about 275 mg to about 300 mg, or about 300 mg to about 325 mg, or about 325 mg to about 350 mg, or about 350 mg to about 375 mg, or about 375 mg to about 400 mg, or about 400 mg to about 425 mg, or about 425 mg to about 450 mg, or about 450 mg to about 475 mg, or about 475 mg to about 500 mg, or about 500 mg to about 525 mg, or about 525 mg to about 550 mg, or about 550 mg to about 575 mg, or about 575 mg to about 600 mg, or about 600 mg to about 625 mg, or about 625 mg to about 650 mg, or about 650 mg to about 675 mg, or about 675 mg to about 700 mg, or about 700 mg to about 725 mg, or about 725 mg to about 750 mg, or about 750 mg to about 775 mg, or about 775 mg to about 800 mg, or at least 50 mg, or at least 75 mg, or at least 100 mg, or at least 125 mg, or at least 150 mg, or at least 175 mg, or at least 200 mg, or at least 225 mg, or at least 250 mg, or at least 275 mg, or at least 300 mg, or at least 325 mg, or at least 350 mg, or at least 375 mg, or at least 400 mg, or at least 425 mg, or at least 450 mg, or at least 475 mg, or at least 500 mg, or at least 525 mg, or at least 550 mg, or at least 575 mg, or at least 600 mg, or at least 625 mg, or at least 650 mg, or at least 650 mg, or at least 675 mg, or at least 700 mg, or at least 725 mg, or at least 750 mg, or at least 775 mg, or at least 800 mg, or at most 50 mg, or at most 75 mg, or at most 100 mg, or at most 125 mg, or at most 150 mg, or at most 175 mg, or at most 200 mg, or at most 225 mg, or at most 250 mg, or at most 275 mg, or at most 300 mg, or at most 325 mg, or at most 350 mg, or at most 375 mg, or at most 400 mg, or at most 425 mg, or at most 450 mg, or at most 475 mg, or at most 500 mg, or at most 525 mg, or at most 550 mg, or at most 575 mg, or at most 600 mg, or at most 625 mg, or at most 650 mg, or at most 650 mg, or at most 675 mg, or at most 700 mg, or at most 725 mg, or at most 750 mg, or at most 775 mg, or at most 800 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 650 mg, or about 675 mg, or about 700 mg, or about 725 mg, or about 750 mg, or about 775 mg, or about 800 mg.

In some embodiments, a daily dose may be the sum of a first dose, a second dose, and a third dose, wherein the daily dose is about 25 mg to about 50 mg, or about 50 mg to about 75 mg, or about 75 mg to about 100 mg, or about 100 mg to about 125 mg, or about 125 mg to about 150 mg, or about 150 mg to about 175 mg, or about 175 mg to about 200 mg, or about 200 mg to about 225 mg, or about 225 mg to about 250 mg, or about 250 mg to about 275 mg, or about 275 mg to about 300 mg, or about 300 mg to about 325 mg, or about 325 mg to about 350 mg, or about 350 mg to about 375 mg, or about 375 mg to about 400 mg, or about 400 mg to about 425 mg, or about 425 mg to about 450 mg, or about 450 mg to about 475 mg, or about 475 mg to about 500 mg, or about 500 mg to about 525 mg, or about 525 mg to about 550 mg, or about 550 mg to about 575 mg, or about 575 mg to about 600 mg, or about 600 mg to about 625 mg, or about 625 mg to about 650 mg, or about 650 mg to about 675 mg, or about 675 mg to about 700 mg, or about 700 mg to about 725 mg, or about 725 mg to about 750 mg, or about 750 mg to about 775 mg, or about 775 mg to about 800 mg, or at least 50 mg, or at least 75 mg, or at least 100 mg, or at least 125 mg, or at least 150 mg, or at least 175 mg, or at least 200 mg, or at least 225 mg, or at least 250 mg, or at least 275 mg, or at least 300 mg, or at least 325 mg, or at least 350 mg, or at least 375 mg, or at least 400 mg, or at least 425 mg, or at least 450 mg, or at least 475 mg, or at least 500 mg, or at least 525 mg, or at least 550 mg, or at least 575 mg, or at least 600 mg, or at least 625 mg, or at least 650 mg, or at least 650 mg, or at least 675 mg, or at least 700 mg, or at least 725 mg, or at least 750 mg, or at least 775 mg, or at least 800 mg, or at most 50 mg, or at most 75 mg, or at most 100 mg, or at most 125 mg, or at most 150 mg, or at most 175 mg, or at most 200 mg, or at most 225 mg, or at most 250 mg, or at most 275 mg, or at most 300 mg, or at most 325 mg, or at most 350 mg, or at most 375 mg, or at most 400 mg, or at most 425 mg, or at most 450 mg, or at most 475 mg, or at most 500 mg, or at most 525 mg, or at most 550 mg, or at most 575 mg, or at most 600 mg, or at most 625 mg, or at most 650 mg, or at most 650 mg, or at most 675 mg, or at most 700 mg, or at most 725 mg, or at most 750 mg, or at most 775 mg, or at most 800 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 650 mg, or about 675 mg, or about 700 mg, or about 725 mg, or about 750 mg, or about 775 mg, or about 800 mg.

In some embodiments of the methods of the invention, the pharmaceutical compositions are delivered as divided doses, which may be two doses (e.g., a first dose and a second dose) where the first dose and second dose of the pharmaceutical compositions are apportioned according to table set forth in FIG. 6. Each of the dosing strategies described in FIG. 6, where dose 1 is first dose and dose 2 is a second dose, represents an exemplary embodiment of the invention.

In some embodiments, the first dose is at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose. In some embodiments, the first dose is at most 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose. In some embodiments, the first dose is about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose.

In some embodiments, the second dose is at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose. In some embodiments, the second dose is at most 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose. In some embodiments, the second dose is about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or 5% of the daily dose.

Polycystic disease, such as polycystic kidney disease or polycystic liver disease, is a genetic disorder, so treatment will optimally occur over the lifetime of the subject. In initiating treatment of polycystic disease, the subject will go through a "titration phase" to establish the maximal dose tolerated by that subject, which is established as a maintenance dose. During the titration phase, the subject can either pursue an up-titration or a down-titration to establish the maintenance dose. In an up-titration approach, the subject will start with a lower dose expected to provide some efficacy, and will increase his/her dose to a dose that can be tolerated. By tolerated or tolerable, it is meant that the complex of effects from the drug treatment and the disease are able to be managed by the subject. In a down-titration approach, the subject will reduce his/her dose to a dose that is efficacious and tolerable. The time period for the titration phase can be a single day up through a month, and during the titration phase, the daily dose may be administered either as a single or as a divided dose.

In some embodiments where the pharmaceutical compositions are administered as divided doses, a first pharmaceutical composition at a first daily dose may be administered for a treatment period of about 1 to 21 days, or about 7 to 14 days, followed thereafter by a second pharmaceutical composition at a second daily dose for a treatment period of about 1 to 21 days, or about 7 to 14 days, where the second daily dose is greater than, less than, or equal to the first daily dose. In an embodiment, the first pharmaceutical composition is the same as the second pharmaceutical composition, both comprising lixivaptan. In some embodiments, the administration of the second pharmaceutical composition at the second daily dose may be followed thereafter by a third pharmaceutical composition at a third daily dose for a treatment period of about 1 to 21 days, or about 7 to 14 days, wherein the third daily dose is greater than, less than, or equal to the first daily dose and/or the second daily dose. In some embodiments, the first daily dose, second daily dose, and third daily dose may be any daily dose described herein (e.g., the embodiments described in FIG. 6).

In some embodiments, a method for treating a polycystic disease in a human subject comprises the steps of: a) administering a pharmaceutical composition comprising lixivaptan to the human at a first divided dose regimen for a first treatment period; b) conducting a urine osmolality test at the about end of the first treatment period; c) comparing the urine osmolality of the human with a predetermined level; d) administering the pharmaceutical composition comprising lixivaptan to the human at a second, increased divided dose regimen for a second treatment period if the urine osmolality of the human is higher than the predetermined level; e) repeating steps b), c), and d) until a maintenance divided dose regimen is achieved, wherein the urine osmolality of the human is equal to or less than the predetermined level. In an embodiment, the first divided dose regimen, the second divided dose regimen, and the maintenance divided dose regimen comprise a first dose and a second dose, wherein the first dose and the second dose are administered to the human in the same day, and the daily dose is the sum of the first dose and the second dose. In an embodiment, the daily dose of the second divided dose regimen is higher than the daily dose of the first divided dose regimen by a certain amount, wherein the certain amount is selected from the group consisting of 50 mg, 75 mg, 100 mg, 125 mg, 150 mg, 175 mg, 200 mg, 225 mg, 250 mg, 275 mg, 300 mg, 325 mg, 350 mg, 375 mg, and 400 mg. In an embodiment, the predetermined level of urine osmolality is selected from the group consisting of about 500 mOsm/kg, about 475 mOsm/kg, about 450 mOsm/kg, about 425 mOsm/kg, about 400 mOsm/kg, about 375 mOsm/kg, about 350 mOsm/kg, about 325 mOsm/kg, and about 300 mOsm/kg. In an embodiment, the first treatment period or the second treatment period is selected from the group consisting of at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 2 years, and about 3 years. In an embodiment, the first dose and the second dose of the first divided dose regimen are independently selected from the group consisting of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg and about 100 mg. In an embodiment, the first dose and the second dose of the second divided dose regimen are independently selected from the group consisting of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg. In an embodiment, the first dose and the second dose of the maintenance divided dose regimen are independently selected from the group consisting of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg.

In some embodiments, a method for treating a polycystic disease in a human subject comprises the steps of: a) administering a pharmaceutical composition comprising lixivaptan to the human at a first divided dose regimen for a first treatment period; b) conducting a urine specific gravity measurement at the about end of the first treatment period; c) comparing the urine specific gravity of the human with a predetermined level; d) administering the pharmaceutical composition comprising lixivaptan to the human at a second, increased divided dose regimen for a second treatment period if the urine specific gravity of the human is higher than the predetermined level; e) repeating steps b), c), and d) until a maintenance divided dose regimen is achieved, wherein the urine specific gravity of the human is equal to or less than the predetermined level for urine specific gravity. In an embodiment, the first divided dose regimen, the second divided dose regimen, and the maintenance divided dose regimen comprise a first dose and a second dose, wherein the first dose and the second dose are administered to the human in the same day, and the daily dose is the sum of the first dose and the second dose. In an embodiment, the daily dose of the second divided dose regimen is higher than the daily dose of the first divided dose regimen by a certain amount, wherein the certain amount is selected from the group consisting of 50 mg, 75 mg, 100 mg, 125 mg, 150 mg, 175 mg, 200 mg, 225 mg, 250 mg, 275 mg, 300 mg, 325 mg, 350 mg, 375 mg, and 400 mg. In an embodiment, the predetermined level of urine specific gravity is between about 1.000 and about 1.025. In an embodiment, the predetermined level of urine specific gravity is selected from the group consisting of about 1.000, 1.005, 1.01, 1.015, 1.02, and 1.025. In an embodiment, the first treatment period or the second treatment period is selected from the group consisting of at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 2 years, and about 3 years. In an embodiment, the first dose and the second dose of the first divided dose regimen are independently selected from the group consisting of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg and about 100 mg. In an embodiment, the first dose and the second dose of the second divided dose regimen are independently selected from the group consisting of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg. In an embodiment, the first dose and the second dose of the maintenance divided dose regimen are independently selected from the group consisting of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg.

In some embodiments, lixivaptan, after a maintenance dose is established for a subject, may be administered for the lifetime of the subject. The maintenance dose can be adjusted during the lifetime of the subject to sustain an acceptable therapeutic ratio.

Regarding the methods of the invention, it has been shown that urine osmolality ($U_{osm}$) is a suitable pharmacodynamic marker for efficacy in PKD. The FDA supported suppression of $U_{osm}$ at or below 300 mOsm/kg as a clinical marker for a therapeutic effect by tolvaptan on PKD (see, e.g., Devuyst, et al., *J. Am. Soc. Nephrol.* (2016) 28:1-11). This value can be reported as "Spot Urine Osmolality" at different time points (e.g. 1, 2, 4, 6, 8, 10, 12, 16, 24 hours) after administration of the drug.

Other measures of efficacy of lixivaptan in treating PKD are: urine osmolality area under the curve (AUC) for a 24 hour or 7 day treatment, urine volume; duration that $U_{osm}$ remains below, for example, 300 mOsm/kg over a specified time period; urine voids during awake periods; average number of daily urine voids during awake periods; urine voids during normal sleep periods; average number of daily urine voids during normal sleep periods; serum vasopressin levels; serum osmolality; serum copeptin levels urine copeptin levels; urinary HB-EGF; and quantity and/or quality of urinary exosomes or urinary extracellular vesicles.

Lixivaptan, at doses similar to those used to treat PKD with tolvaptan, has been found not to reduce $U_{osm}$ to levels below 300 mOsm/kg uninterruptedly over 24 hours in humans. Thus, levels higher than tolvaptan were studied, and it was unexpectedly found that higher levels of lixivaptan over a prolonged treatment period could suppress urine osmolality to acceptable levels while not causing any significant liver toxicity. In some embodiments, doses of lixivaptan equal to or greater than 200 mg daily delivered in a divided dose regimen are effective. In some embodiments, doses of lixivaptan between 250 mg and 500 mg daily delivered in a divided dose regimen are effective. In some embodiments, doses of lixivaptan between 250 mg and 400 mg daily delivered in a divided dose regimen are effective.

During clinical studies and the titration phase for a subject, it is useful to identify doses of lixivaptan administered to a human subject which reduce $U_{osm}$ to levels of at or below about 200 mOsm/kg to about 400 mOsm/kg. During the maintenance phase of the methods described herein, $U_{osm}$ will fluctuate and may vary depending on a number of factors. At any given time point in the course of titration phase or maintenance dosing, the $U_{osm}$ of a subject dosing with lixivaptan could be between about 200 to about 400 mOsm/kg. In some embodiments, the $U_{osm}$ level in a subject should be at or below about 400 mOsm/kg, or about 375 mOsm/kg, or about 350 mOsm/kg, or about 325 mOsm/kg, or about 300 mOsm/kg, or about 275 mOsm/kg, or about 250 mOsm/kg, or about 225 mOsm/kg, or about 200 mOsm/kg.

In some embodiments, the methods of the invention include administering a therapeutically effective amount of a pharmaceutical composition comprising lixivaptan, or a pharmaceutically acceptable salt, prodrug, solvate, cocrystal, conformer, polymorph, crystalline form, tautomer, or hydrate thereof, and a pharmaceutically acceptable carrier, to the human subject, wherein liver function of the subject is not impaired. It has been determined that lixivaptan does not cause liver impairment at the doses described herein for the treatment of PKD in the titration phase and maintenance dosing. Liver impairment can be assessed by measuring a subject's serum alanine transferase (ALT) enzyme levels; levels greater than or equal to three times the upper limit of normal (ULN), a level considered clinically significant as part of the Hy's law criteria, for the subject treated with the pharmaceutical composition for at least 7 days would be associated with liver impairment.

In an embodiment, lixivaptan may advantageously be administered for the treatment of polycystic disease by the use of a divided-dose regimen, in which unit doses of either the same amount or differing amounts of lixivaptan are administered to a human twice daily, preferably a first dose in the morning and a second dose in the afternoon or evening. In one embodiment, the first dose is greater than the second dose. In an embodiment, the first dose is between 175 and 250 mg, 180 and 240 mg, 185 and 230 mg, 190 and 220 mg, 195 and 210 mg, or 195 and 205 mg, and the second dose is between 75 and 150 mg, 80 and 140 mg, 85 and 130 mg, 90 and 120 mg, 95 and 110 mg, or 95 and 105 mg. In an embodiment, the first dose is 250 mg and the second dose is 150 mg. In an embodiment, the first dose is 150 mg and the second dose is 50 mg. In an embodiment, the first dose is 200 mg and the second dose is 100 mg. In an embodiment, the first dose is 50 mg and the second dose is 50 mg. In an embodiment, the first dose is 200 mg and the second dose is 200 mg. In an embodiment, the first dose is 100 mg and the second dose is 100 mg. In an embodiment, the second dose is administered about 8 hours later than the first dose. In an embodiment, the second dose is administered about 9 hours later than the first dose. In an embodiment, the second dose is administered about 10 hours later than the first dose. In an embodiment, the second dose is administered about 11 hours later than the first dose. In an embodiment, the second dose is administered about 12 hours later than the first dose. In some embodiments, polycystic disease is polycystic kidney disease (PKD) or poly cystic liver disease.

In an embodiment, a pharmaceutical composition comprising lixivaptan may advantageously be administered for the treatment of polycystic disease by the use of a divided-dose regimen, in which unit doses of either the same amount or differing amounts of lixivaptan are administered to a human twice daily, preferably a first dose in the morning and then a second dose in the afternoon or evening. In one embodiment, the first dose is greater than the second dose. In an embodiment, the first dose is between 175 and 250 mg, 180 and 240 mg, 185 and 230 mg, 190 and 220 mg, 195 and 210 mg, or 195 and 205 mg, and the second dose is between 75 and 150 mg, 80 and 140 mg, 85 and 130 mg, 90 and 120 mg, 95 and 110 mg, or 95 and 105 mg. In an embodiment, the first dose is 250 mg and the second dose is 150 mg. In an embodiment, the first dose is 250 mg and the second dose is 150 mg. In an embodiment, the first dose is 150 mg and the second dose is 50 mg. In an embodiment, the first dose is 200 mg and the second dose is 100 mg. In an embodiment, the first dose is 50 mg and the second dose is 50 mg. In an embodiment, the first dose is 200 mg and the second dose is 200 mg. In an embodiment, the first dose is 100 mg and the second dose is 100 mg. In an embodiment, the second dose is administered about 8 hours later than the first dose. In an embodiment, the second dose is administered about 9 hours later than the first dose. In an embodiment, the second dose is administered about 10 hours later than the first dose. In an embodiment, the second dose is administered about 11 hours later than the first dose. In an embodiment, the second dose is administered about 12 hours later than the first dose. In some embodiments, polycystic disease is polycystic kidney disease (PKD) or poly cystic liver disease.

In an embodiment, a pharmaceutical composition comprising lixivaptan may advantageously be administered for the treatment of polycystic disease by the use of a divided-dose regimen, in which unit doses of either the same amount or differing amounts of lixivaptan are administered to a human three times daily, preferably a first dose in the morning, then a second dose in the afternoon, then a third dose in the evening. In an embodiment, the first dose is between 175 and 250 mg, 180 and 240 mg, 185 and 230 mg, 190 and 220 mg, 195 and 210 mg, or 195 and 205 mg; the second dose is between 75 and 150 mg, 80 and 140 mg, 85 and 130 mg, 90 and 120 mg, 95 and 110 mg, or 95 and 105 mg; and the third dose is between 75 and 150 mg, 80 and 140 mg, 85 and 130 mg, 90 and 120 mg, 95 and 110 mg, or 95 and 105 mg. In an embodiment, the first dose is 100 mg, the second dose is 100 mg, and the third dose is 100 mg. In an embodiment, the first dose is 150 mg, the second dose is 100 mg, and the third dose is 75 mg. In an embodiment, the first dose is 200 mg, the second dose is 75 mg, and the third dose is 75 mg. In an embodiment, the second dose is administered about 6 hours later than the first dose. In an embodiment, the second dose is administered about 7 hours later than the first dose. In an embodiment, the second dose is administered about 8 hours later than the first dose. In an embodiment, the third dose is administered about 6 hours later than the second dose. In an embodiment, the third dose is administered about 7 hours later than the second dose. In an embodiment, the third dose is administered about 8 hours later than the second dose. In some embodiments, polycystic disease is polycystic kidney disease (PKD) or poly cystic liver disease.

In some embodiments of the methods described herein, a pharmaceutical composition (e.g., a first pharmaceutical composition and optionally a second and/or third pharmaceutical composition) may be administered to a human subject during the titration phase at least 1 to 14 days, or at least 2 to 14 days, or at least 3 to 14 days, or at least 4 to 14 days, or at least 5 to 14 days, or at least 6 to 14 days, or at least 7 to 14 days, or at least 1 day, or at least 2 days, or at least 3 days, or at least 4 days, or at least 5 days, or at least 6 days, or at least 1 week, or at least 2 weeks, or at least 3 weeks, or at least 1 month, or at most 2 months, or at least 3 months, or at least 4 months, or at least 5 months, or at least 6 months. The pharmaceutical composition established as a maintenance dose can be administered following the titration phase, for at least 2 to 14 days, or at least 3 to 14 days, or at least 4 to 14 days, or at least 5 to 14 days, or at least 6 to 14 days, or at least 7 to 14 days, or at least 1 day, or at least 2 days, or at least 3 days, or at least 4 days, or at least 5 days, or at least 6 days, or at least 1 week, or at least 2 weeks, or at least 3 weeks, or at least 1 month, or at most 2 months, or at least 3 months, or at least 4 months, or at least 5 months, or at least 6 months, or at least 7 months, or at least 8 months, or at least 9 months, or at least 10 months, or at least 11 months, or at least 1 year, or at least 3 years, or at least 5 years, or at least 10 years, or at least 15 years, or at least 20 years, or at least 25 years, or at least 30 years, or at least 35 years, or for the life of the subject.

The amounts of lixivaptan or a pharmaceutical composition comprising lixivaptan as described herein administered will be dependent on the human or mammal being treated, the severity of polycystic disease (e.g., polycystic kidney disease or polycystic kidney disease), the route of administration, the disposition of the lixivaptan formulation, and the discretion of the prescribing physician. Determination of dosing for individual subjects, such as pediatric subjects, can be optimized based on the age of the patient, the size of patient, his/her particular bioavailability/ability to absorb the medication, and his/her metabolism (e.g. efficiency of liver metabolism), distribution (e.g. fat or extracellular water), and excretion (e.g. kidney, GI tract). Pediatric subjects, especially young children, may absorb more drug across the skin or other biological barriers more easily. Their gastric pH may be less acidic, which can affect bioavailability of lixivaptan. Doses for pediatric subjects may be calculated by using Clark's rule (child's weight divided by 150 lbs) or Young's rule (divide the child's age by the sum of the child's age+12). In some embodiments, the invention includes the doses described herein as revised for the treatment of children using either Clark's rule or Young's rule.

An effective dosage of lixivaptan or a pharmaceutical composition thereof is in the range of about 2 to about 20 mg per kg body weight per day, such as about 5 to about 15 mg/kg/day, in single or divided doses. The dosage of lixivaptan or a pharmaceutical composition thereof described herein may be provided in units of mg/kg of body mass or in mg/m$^2$ of body surface area.

An effective amount of lixivaptan or a pharmaceutical composition comprising lixivaptan described herein may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Pharmaceutical Compositions

In an embodiment, the invention provides a pharmaceutical composition for use in the treatment of polycystic disease (e.g., polycystic kidney disease or polycystic liver disease), as described herein.

The pharmaceutical compositions are typically formulated to provide a therapeutically effective amount of lixivaptan or a pharmaceutical composition comprising lixivaptan, as described herein, or a pharmaceutically acceptable salt, solvate, conformer, polymorph, crystalline form, tautomer, cocrystal, or hydrate thereof, as the active ingredient. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

In some embodiments, a pharmaceutical composition can be provided in bulk or in unit dose (or dosage unit) form. A "unit dose" is the amount of a pharmaceutical composition administered to a patient in a single dose. It is especially advantageous to formulate pharmaceutical compositions in unit dose form for ease of administration and uniformity of dosage. A unit dose as used herein refers to physically discrete units suited as unitary dosages for the subject to be treated; each unit containing a predetermined quantity of lixivaptan calculated to produce the desired therapeutic effect in association with an acceptable pharmaceutical carrier. A unit dose form can be packaged as an ampoule, a vial, a suppository, a dragee, a tablet, a capsule, or an IV bag.

The pharmaceutical compositions described herein are preferably for use in the treatment of polycystic disease and, in some embodiments, polycystic kidney disease (PKD) or polycystic liver disease. In some embodiments, the polycystic disease may be polycystic kidney disease (PKD), which may be autosomal dominant polycystic kidney disease (ADPKD) or autosomal recessive polycystic kidney disease (ARPKD).

In some embodiments, the concentration of lixivaptan provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of lixivaptan provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of lixivaptan provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of lixivaptan provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

The exact dosage of lixivaptan will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In some embodiments, the invention provides a pharmaceutical composition for oral administration containing lixivaptan, and a pharmaceutical excipient suitable for administration.

In some embodiments, the invention provides a solid pharmaceutical composition for oral administration containing: (i) an effective amount of lixivaptan, and (ii) a pharmaceutical excipient suitable for administration. In some embodiments, the composition further contains (iii) an effective amount of an additional active pharmaceutical ingredient. For example, additional active pharmaceutical ingredients, as used herein, may include one or more compounds that reduce urine osmolality or are useful in the treatment of polycystic disease (e.g., polycystic kidney disease or polycystic liver disease).

In some embodiments, the pharmaceutical composition may be a liquid pharmaceutical composition suitable for oral consumption.

Pharmaceutical compositions of the invention suitable for oral administration can be presented as discrete dosage forms, such as capsules, granules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, E-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the invention provides a pharmaceutical composition for injection containing lixivaptan, and a pharmaceutical excipient suitable for injection. Components and amounts of compounds in the compositions are as described herein.

The forms in which the compositions of the invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating lixivaptan in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In preferred embodiments, the invention provides a pharmaceutical composition for transdermal delivery containing lixivaptan, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of lixivaptan described herein in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Controlled Release, Sustained Release, and Extended Release Pharmaceutical Formulations The present invention further provides controlled-release, sustained-release, or extended-release therapeutic dosage forms for one or more of the pharmaceutical compositions described herein, in which the composition is incorporated into a delivery system. This dosage form controls release of the lixivaptan in such a manner that a therapeutically effective concentration of lixivaptan is maintained over an extended period of time, with the concentration remaining relatively constant, to improve therapeutic results. Additionally, a controlled-release system would provide minimum peak to trough fluctuations in levels of the lixivaptan.

Exemplary controlled release, sustained release, and extended release formulations, and methods of making the same, are provided in U.S. Pat. Nos. 9,289,389, and 9,408,806, the entirety of which are incorporated herein by reference.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of lixivaptan or a pharmaceutical composition of lixivaptan can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Lixivaptan herein can also be administered intraadiposally or intrathecally.

Exemplary parenteral administration forms include solutions or suspensions of lixivaptan in sterile aqueous solutions, for example, aqueous propylene glycol or dextrose solutions. Such dosage forms can be suitably buffered, if desired.

The invention also provides kits. The kits include lixivaptan in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, lixivaptan and another active pharmaceutical ingredient are provided as separate compositions in separate containers within the kit. In some embodiments, the lixivaptan and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The kits described above are preferably for use in the treatment of the diseases and conditions described herein.

In a particular embodiment, the kits described herein are for use in the treatment of polycystic disease. In some embodiments, the kits described herein are for use in the treatment of polycystic kidney disease (PKD) or polycystic liver disease. In some embodiments, the kits described herein are for use in the treatment of autosomal dominant polycystic kidney disease (ADPKD).

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—In-Clinic Pharmacokinetic Study

The primary objective of this study was to assess the pharmacokinetics and dose proportionality of lixivaptan over the dose range targeted for clinical use (e.g., 100 to 400 mg daily) using unit doses of 50 mg and multiples thereof given twice daily for 7.5 days.

This dose proportionality study had an open-label, multiple-dose, parallel-group design. Subjects received lixivaptan at total daily doses of 100 mg, 200 mg, or 400 mg (administered as 50, 100, and 200 mg Q12H). Subjects were to be enrolled into the study in two cohorts of 30 subjects, but actual cohort numbers were 23 and 34 subjects. Of the 57 subjects enrolled in the study, 27 were female (47.4%) and 30 were male (52.6%). The majority of subjects were White (35/57, 61.4%) and of Hispanic or Latino ethnicity (46/57, 80.7%). The overall mean age of subjects in the study was 33.6 (8.31) years, and the overall mean body mass index for subjects was 26.2 (3.79). There were to be approximately 20 subjects enrolled per dose level. An approximately equal number of males and females were enrolled at each dose level such that neither gender was represented by fewer than 8 subjects. The starting date for each cohort subjects was staggered by 7 days for logistical purposes. Screening evaluations were performed within 28 days prior to Day 1.

Lixivaptan Medication and Dosing

The following doses of lixivaptan were administered to subjects in this study: (a) Lixivaptan 100 mg, administered as 50 mg [1×50 mg capsule] every 12 hours×15 doses; (b) lixivaptan 200 mg, administered as 100 mg [2×50 mg capsules] every 12 hours×15 doses; and (c) Lixivaptan 400 mg, administered as 200 mg [4×50 mg capsules] every 12 hours×15 doses.

The study medication (lixivaptan 50 mg capsules, Lot No. A03630-002L01) was manufactured by Pharmaceutics International Incorporated (Hunt Valley, Md.). Blister packages had two-part labels that included drug name, dose, and lot number. Study medication was shipped on cold packs with temperature monitors. Study medication was stored between 2 and 8° C. and was protected from any extreme conditions of temperature, light, or humidity. Capsules were brought to room temperature prior to administration.

Subjects reported to the clinic one day prior to study medication administration (Day −1) and remained in the clinic until after the 264-hour blood sample was obtained on Day 12. Subjects returned to the clinic on Days 15, 22, and 29 for follow-up and collection of additional blood samples.

Prior to the morning doses of lixivaptan on Days 1 and 8, subjects fasted for approximately 10 hours prior to lixivaptan administration and 4 hours after lixivaptan administration. All other doses were administered under fasting conditions, either 2 hours before or 2 hours after meals. The study medication was administered with 240 milliliters (mL) room temperature water. Subjects were not to receive any oral fluids, other than those used to administer the dose, for 1 hour before and 1 hour after dose administration. Subjects remained sitting or semi-supine, except to void, for 6 hours following the first two doses. While in the clinic, the subjects refrained from strenuous physical activity.

Spot urine collections for urine osmolality determinations were obtained during the clinic stay and at the end of study (EOS). Subjects were asked to completely empty their bladders 15 minutes prior to each scheduled spot urine collection after which each subject had a maximum of 30 minutes to provide a spot urine specimen for osmolality determination. However, it was noted that some subjects were unable to void on demand 15 minutes prior to the scheduled spot urine sampling, so spot urine collections for such subjects were collected at the same time as the bladder void as opposed to 15 minutes following bladder void.

Spot urine osmolality was evaluated at different times during the day. Subjects were asked to completely empty their bladders 15 minutes prior to each scheduled spot urine collection after which each subject had a maximum of 30 minutes to provide a spot urine specimen for osmolality determination. Urine osmolality evaluated on Days 1, 8, 9, and 29 (end of study) showed a substantial decrease for all 3 dose levels between 1 and 2 hours after dosing on Days 1 and 8. Thereafter, values increased, but remained below baseline values (i.e. Day 1, hour 0 value) at 12 hours after dosing. The mean maximal reduction of urine osmolality occurred at 2 hours after administration of the first dose of lixivaptan on Day 1 and Day 8, regardless of the dose administered. All doses tested provoked a marked reduction in urine osmolality, however, the duration of reduction in urine osmolality increased as the dose level increased, both on Day 1 and on Day 8 of dosing. At 24 hours after dosing on Day 9, values approached baseline levels in the 100 mg lixivaptan group (564.7 versus 587.8 mOsm/kg) while values remained below baseline levels in the 200 mg (465.9 versus 602.7 mOsm/kg) and 400 mg (390.3 versus 600.1 mOsm/kg) groups. A summary of urine osmolality is provided below in Table 1.

TABLE 1

Summary of Urine Osmolality (mOsm/kg) Data by Dose and Visit

| Day | Hour | 100 mg Lixivaptan as 50 mg Q12H[a] | | 200 mg Lixivaptan as 100 mg Q12H | | 400 mg Lixivaptan as 200 mg Q12H | |
|---|---|---|---|---|---|---|---|
| | | n | Mean (SD) | n | Mean(SD) | n | Mean (SD) |
| 1 | 0 | 19 | 587.8 (277.1) | 19 | 602.7 (289.3) | 19 | 600.1 (277.5) |
| | 1 | 19 | 250.9 (200.8) | 19 | 285.9 (245.5) | 19 | 237.4 (164.0) |
| | 2 | 19 | 79.8 (16.37) | 19 | 76.9 (30.62) | 19 | 74.5 (48.70) |
| | 4 | 19 | 150.6 (72.10) | 19 | 136.5 (115.5) | 19 | 91.0 (55.76) |
| | 12 | 19 | 378.7 (168.2) | 19 | 369.9 (191.9) | 19 | 294.1 (160.7) |
| 8 | 0 | 19 | 464.7 (176.8) | 18 | 323.6 (125.3) | 19 | 231.0 (130.9) |
| | 1 | 19 | 222.5 (159.2) | 18 | 156.7 (94.81) | 19 | 106.9 (47.98) |
| | 2 | 19 | 139.1 (79.87) | 18 | 93.9 (38.81) | 19 | 82.3 (21.13) |
| | 4 | 19 | 274.3 (163.2) | 18 | 186.7 (92.09) | 19 | 139.1 (57.14) |
| | 12 | 19 | 447.4 (258.6) | 18 | 334.7 (168.0) | 19 | 219.5 (110.0) |
| 9 | 24 | 19 | 564.7 (244.4) | 18 | 465.9 (199.0) | 19 | 390.3 (162.3) |
| EOS[b] | — | 19 | 805.5 (227.3) | 19 | 694.1 (291.7) | 18 | 704.8 (296.9) |

[a]Q12H = every twelve hours
[b]EOS = end of study

Mean maximum plasma concentration for lixivaptan (the highest concentration observed during a dosing interval, $C_{max}$) and $AUC_{(0-12)}$ values (area under the concentration versus time curve from time 0 to 12 hours following dosing) increased with increasing dose and were also higher on Day 8 than on Day 1 for each dose level. Lixivaptan pharmacokinetic parameters demonstrated proportional kinetics over the dose range of 100 mg to 400 mg administered as 2 divided doses. All 3 dose levels appeared to achieve steady state between Day 3 and Day 6.

Lixivaptan was well tolerated in this study. All adverse events (AEs) were mild, and the most frequently occurring treatment-emergent AEs reported by the 57 enrolled subjects were headache (7 subjects), constipation (3 subjects), and chest discomfort (2 subjects). Only headache (2, 1, and 1 subject in the 100, 200, and 400 mg groups, respectively) and vomiting and asthenia (1 subject each in the 400 mg group) were considered possibly or probably related to study drug. No apparent dose-related trends were observed in type, frequency, or severity of AEs, and with the exception of headache, none of the AEs seen in previous healthy volunteer studies and thought to be related to volume depletion (headache, dizziness, thirst, orthostatic hypotension, and tachycardia) were reported as AEs in the present study. None of the AEs were serious or resulted in death or discontinuation from the study.

Serum osmolality was mildly increased during the study in a dose related manner, but urine osmolality decreased substantially for all 3 dose levels between 1 and 2 hours after dosing on Days 1 and 8 and remained lower than baseline values for up to 12 hours after dosing on those days. Urine output was increased during Days 1-8. Dose-proportional kinetics were observed for lixivaptan across the range of 100 mg to 400 mg (administered as 50 mg to 200 mg every twelve hours). No significant gender-related differences in pharmacokinetic results were observed. Lixivaptan was well tolerated by healthy subjects in this repeat dose pharmacokinetic study.

Percentage of Responders Analysis

An analysis of the data described in Table 1 shows that only approximately 16% of the subjects experienced a full 24 hour suppression of Uosm to 300 mOsm/kg or lower when dosed at 50 mg lixivaptan twice daily (see FIG. 1, where the y-axis is the % of subjects achieving uninterrupted urine osmolality suppression below target level during 24 hours). At 100 mg twice daily, only approximately 46% of the subjects experienced a full 24 hour suppression of $U_{osm}$ to 300 mOsm/kg or lower. At 200 mg twice daily, the % responders was approximately 78%.

Example 2—In Vivo Study of the Effects of Lixivaptan on PCK Rats

A study was performed that examined the effect of lixivaptan (0.5% or 1% w/w lixivaptan in ground rodent chow) on bodyweight, kidney weight, kidney cAMP, urine output, and serum electrolyte concentration in PCK rats, an orthologous animal model of Autosomal Recessive PKD that develops a phenotype reminiscent of ADPKD.

Experimental animals and study design. PCK rats were divided into control and treatment groups at four weeks of age (n=59, ~10 animals per treatment group and gender). Lixivaptan was dissolved in DMSO and added to ground rodent chow (Regrind Labdiet 5053) at 0.5% or 1.0% concentration (w/w) by homogenous mixing, whereas control animals received the same diet without lixivaptan. Animals were exposed to control- or lixivaptan-diet for eight weeks and were sacrificed at twelve weeks of age.

TABLE 2

Apportionment of Control and Treated PCK Rats

| PCK rats | Control (Vehicle) | 0.5% Lixivaptan | 1.0% Lixivaptan |
|---|---|---|---|
| Male | 10 | 10 | 9 |
| Female | 10 | 10 | 10 |

Experimental Protocol. Twenty-four hour urine outputs in metabolic cages were collected twice at 6 and 9 weeks of age (Study week 3 and 6, respectively). At the end of the dosing period, the animals were weighed and anesthetized with ketamine 90 mg/kg and xylazine 10 mg/kg, IP. Blood samples were obtained by cardiac puncture for determination of plasma electrolytes, creatinine and plasma urea levels. The right kidney and part of the liver were placed into pre-weighed vials containing 10% formaldehyde in phosphate buffer (pH 7.4). The tissues were embedded in paraffin for histological studies. The left kidneys were immediately frozen in liquid nitrogen for determination of cAMP.

Cyclic AMP Content of Whole Kidneys

The kidneys were weighed and ground to fine powder under liquid nitrogen in a stainless steel mortar and homogenized in 10 volumes of 0.1M HCl. The protein concentration was measured by using BCA Protein Assay Kit (Pierce, Ill.). After centrifugation at 600 g for 10 min, the supernatant was further diluted in 0.1M HCl and run directly in the assay or stored frozen for later analysis. The cAMP content was assessed by Direct cAMP ELISA kit, according to the manufacturer's instructions (Enzo Life Sciences, Inc. Farmingdale, N.Y.). Samples were taken in triplicate. The results were expressed in pmol/mg of protein.

Statistical Analysis. Comparisons between groups were analyzed using one-way or two-way analysis of variance (ANOVA) with least significant difference comparisons of the means or student's t-test as appropriate. Data were expressed as means±SD.

Results

The results of this study are shown in Table 3, below. PCK rats in the control group showed enlarged kidneys and extensive cyst formation, consistent with the development of a polycystic kidney phenotype. Compared to control animals, PCK rats treated with lixivaptan showed reduced disease manifestations. A beneficial effect of lixivaptan was observed for all aspects of disease tested, including biochemical markers, renal morphology, and renal function. Compared to control animals, PCK rats treated with 0.5% lixivaptan showed a marked reduction in kidney weight as a percentage of body weight (26%; $p<0.008$), and a reduction in kidney cAMP levels (23%; $p=0.016$). As expected, these reductions were associated with statistically significant increases in 24 h urine output during study week 3 (rats at 7 weeks of age; 175%; $p<0.0001$) and study week 6 (rats at 10 weeks of age) (189%, $p<0.0001$) and in serum sodium (1.6%; $p<0.05$) in the 0.5% lixivaptan group. Significant increases in Study week 3 urine output (223%; $p<0.0001$) and Study week 6 urine output (237%; $p<0.001$) were seen in the 1.0% lixivaptan group.

For the ratio of kidney weight over body weight (% kidney weight/body weight) when analyzed across both genders, the 0.5% lixivaptan group showed a statistically significant decrease (1.2%+/−0.3 for lixivaptan and 1.7%+/− for control; $p<0.01$). Treatment with 0.5% lixivaptan was associated with a 26% ($p=0.008$) reduction in relative kidney size and a 54% ($p<0.001$) improvement in cystic phenotype compared to control, and 1.0% lixivaptan was associated with a 25% ($p<0.01$) improvement in cystic phenotype compared to control. In addition, a beneficial effect on kidney fibrosis score trending toward significance (30%, $p=0.12$) was observed in the 0.5% lixivaptan group despite the reported mild nature of fibrosis at this stage of disease. These results were accompanied by a reduction in serum creatinine, a marker for renal function (13.2%, $p<0.001$). The statistical separation between the 1.0% lixivaptan group and control group was negatively impacted by the presence of three outliers in the 1.0% lixivaptan group. The three animals (1 male and 2 females) showed elevated ratios of organ weight vs. body weight for kidney, heart, liver and/or spleen. Removing these three outliers from the 1.0% lixivaptan group and a similar outlier from the control group resulted in a highly significant difference between the 1.0% lixivaptan group and control group for the % kidney weight/body weight comparison (1.6% would become 1.3%; the latter value with $p<0.01$ compared to the control of 1.7%).

In addition to kidney manifestations, the majority of patients with PKD also develop liver cysts and fibrosis. This study assessed whether lixivaptan could ameliorate liver pathology in PCK rats. Compared to control animals, treatment with 0.5% lixivaptan showed a protective effect on the development of disease manifestations in the liver, namely a reduction in (a) liver weight as a percentage of body weight, (b) liver cyst burden, and (c) liver fibrosis. A histomorphometric analysis was conducted to quantitate these treatment effects. Compared to control animals, animals treated with 0.5% lixivaptan showed highly significant reductions in liver cyst score (39%; $p=0.0002$) and trends toward significance for the ratio of liver weight vs. body weight (5.2%; $p=0.08$) and liver fibrosis score (20.6%, $p=0.08$). The 1.0% lixivaptan group did not separate from control. The beneficial effect of lixivaptan on liver pathology was not noted with other vasopressin antagonists in the PCK model (Gattone et al., 2003 Nat Med. 9(10): 1323-6).

For this animal model of PKD, the effect of lixivaptan was greatest in the 0.5% group, whereas the 1.0% group did not perform as consistently in this study. A similar inverse dose-response effect was noted with other agents in the PCK model, including PPARγ agonists (Flaig et al., 2016 J Transl Intern Med. 4: 118-26) and tolvaptan (Wang et al., 2005 J Am Soc Nephrol. 16(4): 846-851). With respect to tolvaptan, it was speculated that antagonism for the vasopressin V1a receptor and inhibition of intracellular calcium release at high concentrations of tolvaptan may limit the potential benefit of higher doses of the drug (Wang et al., 2005). Similar competing factors could contribute to the reduced effect seen with the 1.0% dose of lixivaptan in this study. Without being limited to any one theory of the invention, alternative explanations that are more specific to the results in this study include an imbalance in outliers in the 1.0% lixivaptan group and a potential differential food intake or food liking effect. With regards to the latter, animals in the 1.0% lixivaptan group showed reduced weight gain as compared to control, suggesting reduced food intake and, consequently, potentially reduced dosing.

TABLE 3

Results of In Vivo Rat Lixivaptan Study

| Parameter | Control | | 0.5% Lixivaptan | | 1.0% Lixivaptan | |
|---|---|---|---|---|---|---|
| | M (n = 10) | F (n = 10) | M (n = 10) | F (n = 10) | M (n = 9) | F (n = 10) |
| Body Weight (g) | 457 ± 37 | 260 ± 30 | 434 ± 24 | 254 ± 13 | 403 ± 33 | 236 ± 26 |
| Total Kidney Weight (g) | 7.41 ± 2.00 | 4.35 ± 1.58 | 5.97 ± 2.04 | 2.82 ± 0.33 | 5.92 ± 1.95 | 4.14 ± 2.46 |
| % Kidney/Body Weight | 1.64 ± 0.47 | 1.69 ± 0.70 | 1.37 ± 0.45 | 1.11 ± 0.10* | 1.47 ± 0.46 | 1.75 ± 0.99 |
| Kidney Cyst Score (%) | 17.7 ± 6.0 | 14.2 ± 4.4 | 7.7 ± 1.7*** | 7.1 ± 4.2** | 12.0 ± 3.7* | 11.9 ± 3.1 |

TABLE 3-continued

Results of In Vivo Rat Lixivaptan Study

| | | | | | | |
|---|---|---|---|---|---|---|
| Kidney Fibrosis Score (%) | 3.3 ± 2.0 | 2.2 ± 2.0 | 1.8 ± 1.2 | 2.0 ± 1.1 | 2.9 ± 1.3 | 2.1 ± 0.8 |
| cAMP (pmol/mg protein) | 19.2 ± 4.2 | 21.6 ± 7.8 | 16.5 ± 5.1 | 15.0 ± 4.6* | 24.0 ± 12.0 | 23.6 ± 8.1 |
| 24 hr urine week 7 (ml) | 16.5 ± 6.3 | 12.3 ± 2.7 | 45.5 ± 9.1*** | 33.5 ± 8.6*** | 53.9 ± 7.4*** | 39.7 ± 14.2*** |
| 24 hr urine week 10 (ml) | 23.1 ± 5.0 | 13.1 ± 4.5 | 53.5 ± 14.3*** | 47.7 ± 16.8*** | 63.7 ± 10.1*** | 54.8 ± 19.3*** |
| Plasma Creatinine (mg/dl) | 0.74 ± 0.07 | 0.72 ± 0.06 | 0.63 ± 0.07** | 0.64 ± 0.08** | 0.67 ± 0.04* | 0.68 ± 0.06 |
| Plasma Urea (mg/dl) | 34.9 ± 16.4 | 41.8 ± 16.3 | 32.2 ± 5.8 | 32.3 ± 3.9 | 32.3 ± 5.0 | 37.7 ± 10.5 |
| Plasma Sodium (mEq/L) | 142 ± 3 | 145 ± 3 | 147 ± 4** | 145 ± 2 | 147 ± 1*** | 143 ± 3 |
| Plasma Potassium (mEq/L) | 6.3 ± 0.53 | 6.3 ± 0.95 | 6.3 ± 0.42 | 6.0 ± 0.9 | 6.1 ± 0.9 | 6.9 ± 0.9 |
| Liver Weight (g) | 25.8 ± 4.1 | 16.0 ± 2.4 | 23.8 ± 2.3 | 14.5 ± 1.6 | 22.5 ± 2.7* | 16.8 ± 6.7 |
| % Liver/Body Weight | 5.67 ± 0.55 | 6.15 ± 0.70 | 5.49 ± 0.44 | 5.72 ± 0.42 | 5.60 ± 0.61 | 7.11 ± 2.61 |
| Liver Cyst Score (%) | 5.5 ± 2.0 | 6.0 ± 2.2 | 3.2 ± 1.6 | 3.7 ± 0.8 | 5.8 ± 1.3 | 6.2 ± 2.7 |
| Liver Fibrois Score (%) | 3.9 ± 1.7 | 3.3 ± 1.6 | 3.1 ± 1.1 | 2.7 ± 0.3 | 4.2 ± 2.0 | 4.1 ± 1.4 |

| | 2 x 3 ANOVA (p-values) | | |
|---|---|---|---|
| Parameter | Gender | Treatment LD | Treatment HD |
| Body Weight (g) | 0.0001*** | 0.14 | 0.0009*** |
| Total Kidney Weight (g) | 0.0001*** | 0.0069** | 0.20 |
| % Kidney/Body Weight | 0.89 | 0.0078** | 0.78 |
| Kidney Cyst Score (%) | 0.14 | 0.0001*** | 0.0083** |
| Kidney Fibrosis Score (%) | 0.13 | 0.12 | 0.64 |
| cAMP (pmol/mg protein) | 0.93 | 0.0160* | 0.23 |
| 24 hr urine week 7 (ml) | <0.0001*** | <0.0001*** | <0.0001*** |
| 24 hr urine week 10 (ml) | <0.0001*** | <0.0001*** | <0.0001*** |
| Plasma Creatinine (mg/dl) | 0.96 | 0.0002*** | 0.0041** |
| Plasma Urea (mg/dl) | 0.15 | 0.10 | 0.41 |
| Plasma Sodium (mEq/L) | 0.32 | 0.0289* | 0.14 |
| Plasma Potassium (mEq/L) | 0.37 | 0.55 | 0.46 |
| Liver Weight (g) | 0.0001*** | 0.059 | 0.39 |
| % Liver/Body Weight | 0.0209* | 0.079 | 0.34 |
| Liver Cyst Score (%) | 0.38 | 0.0002*** | 0.69 |
| Liver Fibrois Score (%) | 0.36 | 0.08 | 0.29 | vs control *p <0.05; p <0.01; * p <0.001

Example 3—Study of Lixivaptan in Renally Impaired Patients

A clinical study was undertaken to determine the pharmacokinetics (PK) of lixivaptan in renally impaired subjects. In this study, the PK of lixivaptan following a single 100 mg oral dose of lixivaptan was evaluated in subjects with end-stage renal disease (ESRD) and control subjects with normal renal function. Pharmacodynamic (PD) evaluations, including vasopressin concentration, serum sodium concentration, urine volume, and urine osmolality were assessed. Overall total lixivaptan exposure was, on average, 32 and 31% lower in ESRD subjects compared to subjects with normal renal function, as assessed by AUC0-∞ and AUC0-t, respectively. Similarly, peak total lixivaptan concentrations were, on average, 31% lower in subjects with ESRD. The PK results of such study are shown in Table 4. Results of urine osmolality measurements are shown in Table 5.

TABLE 4

Summary of Pharmacokinetic Evaluations

| Parameter | Statistics | Normal | ESRD |
|---|---|---|---|
| AUC - ∞ (ng · hr/mL) | n | 11 | 12 |
| | Mean | 1287 | 856 |
| | SD | 618 | 336 |
| | CV % | 48 | 39.2 |
| AUC 0-t (ng · hr/mL) | n | 12 | 12 |
| | Mean | 1200 | 809 |
| | SD | 604 | 344 |
| | CV % | 50.4 | 42.5 |
| Cmax (ng/mL) | n | 12 | 12 |
| | Mean | 383 | 238 |
| | SD | 271 | 83.6 |
| | CV % | 70.9 | 35.1 |
| CL/F (L/hr) | n | 11 | 12 |
| | Mean | 94.2 | 137 |
| | SD | 40.1 | 59.8 |
| | CV % | 42.6 | 43.7 |
| Lambdaz(hr-1) | n | 11 | 12 |
| | Median | 0.06035 | 0.05752 |
| | Min-Max | 0.0308 - 0.0857 | 0.0273 - 0.1019 |
| t1/2 (hr) | n | 11 | 12 |
| | Median | 12.03 | 13.325 |
| | Min-Max | 8.09 - 22.49 | 6.80 - 25.43 |
| tmax (hr) | n | 12 | 12 |
| | Median | 1 | 1 |
| | Min-Max | 0.50 - 1.50 | 0.50 - 3.00 |
| VZ/F (L) | n | 11 | 12 |
| | Mean | 1750 | 2740 |
| | SD | 1010 | 1620 |
| | CV % | 57.6 | 59.2 |

TABLE 5

Results of Lixivaptan Therapy in Renally Impaired Patients

| Parameter | Scheduled Interval | Evaluation | Statistics | Normal n = 12 | ESRD n = 12 |
|---|---|---|---|---|---|
| Urine osmolality (mosmol/ kg) | Predose | Observed | n | 11 | 7 |
| | | | Mean | 514.7 | 311.1 |
| | | | SD | 289.10 | 36.07 |
| | 0 to 2 hours | Observed | n | 12 | 4 |
| | | | Mean | 132.6 | 216.5 |

TABLE 5-continued

Results of Lixivaptan Therapy in Renally Impaired Patients

| Parameter | Scheduled Interval | Evaluation | Statistics | Normal n = 12 | ESRD n = 12 |
|---|---|---|---|---|---|
| | postdose | | SD | 72.58 | 44.83 |
| | | Change from baseline | n | 11 | 3 |
| | | | Mean | −398.5 | −109.0 |
| | | | SD | 253.43 | 60.51 |
| | 2 to 4 hours postdose | Observed | n | 12 | 7 |
| | | | Mean | 109.9 | 202.4 |
| | | | SD | 52.14 | 53.35 |
| | | Change from baseline | n | 11 | 7 |
| | | | Mean | −412.6 | −108.7 |
| | | | SD | 266.71 | 59.71 |
| | 4 to 8 hours postdose | Observed | n | 12 | 8 |
| | | | Mean | 272.8 | 195.1 |
| | | | SD | 165.37 | 34.15 |
| | | Change from baseline | n | 11 | 7 |
| | | | Mean | −258.3 | −118.3 |
| | | | SD | 252.74 | 48.00 | n = number of subjects/subjects in a sample from a population or analysis group
SD = standard deviation In marked contrast to tolvaptan, which showed increased exposure in subjects with impaired renal function compared to healthy individuals (Shoaf, 2013), lixivaptan exposure in the ESRD dialysis patients was lower than in normal subjects. Total lixivaptan exposure was 32% and 31% lower in ESRD subjects compared to subjects with normal renal function, as assessed by AUC0-∞ and AUC0-t, respectively. Similarly, peak total lixivaptan concentrations were, on average, 31% lower in subjects with ESRD. Single doses of lixivaptan were well tolerated in both groups and no safety issues were identified. The known PD effects of lixivaptan were confirmed in the study, in that it functioned as an aquaretic through V2 receptor blockade, resulting in elevations of vasopressin levels in both renal function groups, as well as increased urine output and decreased urine osmolality in the normal group. However, the effect of lixivaptan on change from baseline in urine osmolality was markedly reduced in the ESRD group.

Example 4—$U_{OSM}$ Study in a Variety of Subjects

Clinical studies conducted with lixivaptan in healthy subjects and various patient populations (patients with hypervolemic and euvolemic hyponatremia and patients with End Stage Renal Disease) demonstrated that treatment with lixivaptan readily suppressed urinary osmolality to levels below the target threshold of 300 mOsm/kg, irrespective of the specific patient population tested.

Healthy Volunteers

Figure 3:
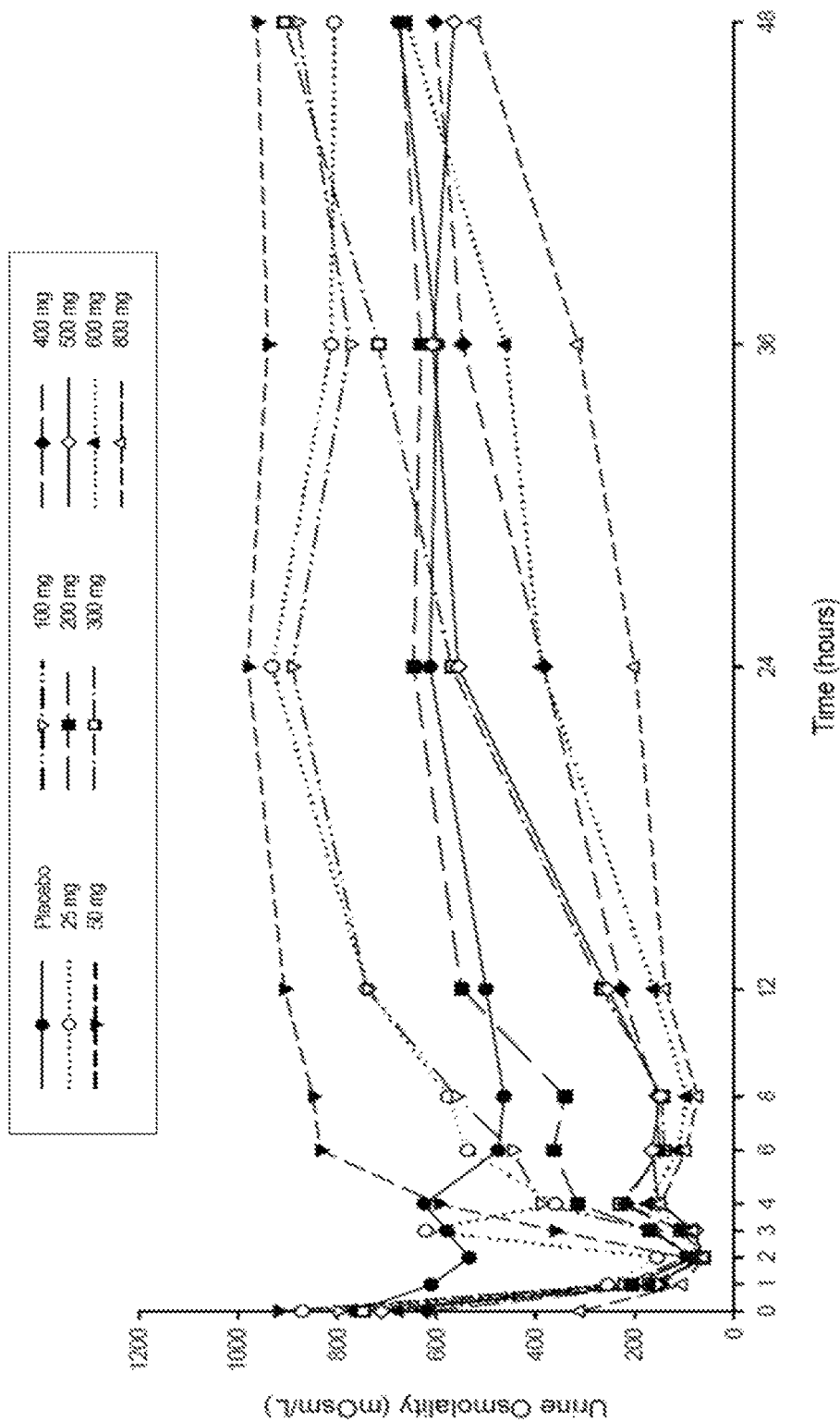
FIG. 3 illustrates the time course of mean $U_{osm}$ on day 14 following single oral doses of lixivaptan in healthy volunteers.

Lixivaptan in healthy volunteers was tested in a randomized, double-blind, placebo-controlled, ascending multiple-dose, safety and tolerance clinical study in 98 healthy male subjects. FIG. 3 shows the time course of mean $U_{osm}$ on Day 14 following a single oral dose of lixivaptan.

SIADH Patients

Figure 4:
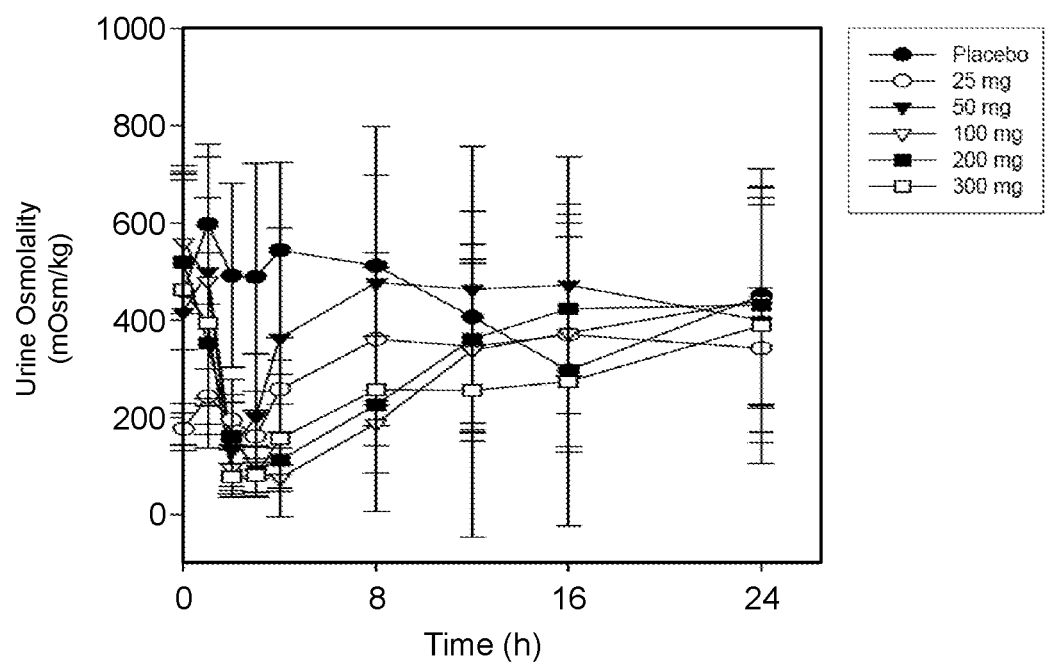
FIG. 4 illustrates the time course of mean $U_{osm}$ on day 1 following a single oral dose of lixivaptan in patients with Syndrome of Inappropriate Anti-Diuretic Hormone.
Figure 5:
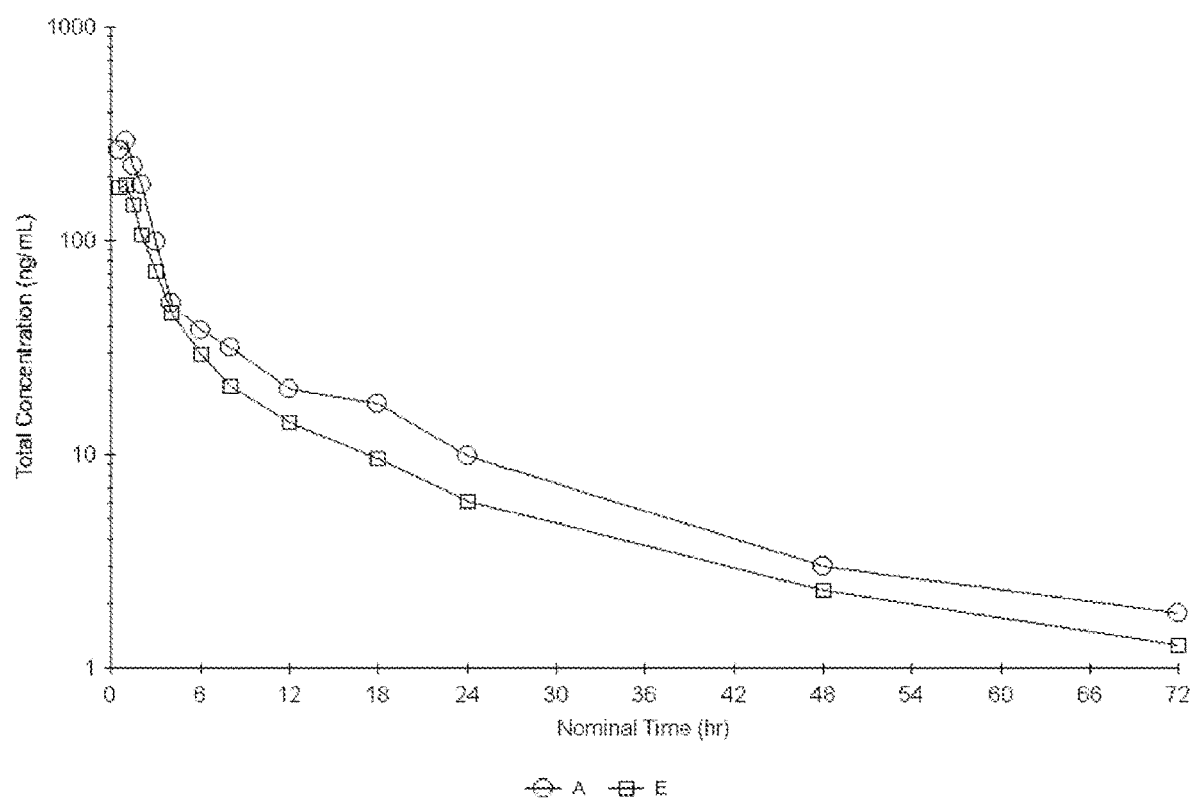
FIG. 5 illustrates the pharmacokinetic profile of lixivaptan in healthy volunteers compared to patients with End Stage Renal Disease.

Subjects with Syndrome of Inappropriate Anti-Diuretic Hormone (SIADH) secretion were tested in a randomized, double-blind, placebo-controlled, ascending single-dose, safety and tolerance study. FIG. 4 shows the time course of mean $U_{osm}$ on Day 1 following a single oral dose of lixivaptan in this patient population.

Example 5—Liver Effects of Lixivaptan

A simulation study was undertaken to assess the potential for liver injury from lixivaptan, using techniques reported previously for tolvaptan (Woodhead J L et al., 2017 Toxicol Sci. 155(1), 61-74). Starting with a panel of in vitro assay data and clinical data, this approach used a mathematical, mechanistic modeling software to assess the liver toxicity risk of lixivaptan.

The results of the simulations indicated that lixivaptan would not cause liver toxicity, confirming the clinical observations reported in the trials described above (e.g., no clinically relevant ALT elevations were attributable to lixivaptan after simulated 100 mg BID dosing for 60 days). The simulation also indicated that there would be no serum alanine transferase (ALT) elevations>3× ULN (upper limit of normal) observed at 200/100 mg split daily dosing of lixivaptan for 12 weeks. It was reported by Woodhead that approximately 8% of individuals would have ALT elevations after 90/30 mg split daily dosing with tolvaptan. At a dosage of 400 mg BID of lixivaptan for 7 days, the simulation reported only rare (2.46%) ALT elevations>3× ULN, none of which had features that suggested a clinical concern. These simulation results are conservative since no ALT elevations were noted when 67 individuals were treated with 400 mg BID doses of lixivaptan for 7 days.

The results of the simulation are consistent with the intrinsic chemical differences between lixivaptan and tolvaptan. It has been observed that drugs with a coefficient of partition (Log P) greater than 3.0 are disproportionately associated with the potential to cause liver injury (Chen M. et al., 2013 Hepatology 58 (1), 388-396). The measured Log P value for tolvaptan is greater than 3.0, which is consistent with the clinical finding of liver toxicity associated with tolvaptan. Surprisingly, despite the chemical similarity with tolvaptan, the measured Log P value for lixivaptan is 1.0. This suggests that lixivaptan does not belong to the group of drugs that are associated with high risk of liver toxicity.

Example 6—Clinical PK/PD Study in ADPKD Patients

Doses of lixivaptan in the range from 200 to 400 mg can be administered to ADPKD patients in a divided dose regimen depicted in Table 6. Urine osmolality, serum osmolality, serum vasopressin, serum copeptin, urine copeptin, urinary HB-EGF, urinary exosomes or urinary extracellular vesicles can be measured.

TABLE 6

Study Parameters

| Study Groups | Study Period 1 | Wash-out | Study Period 2 |
|---|---|---|---|
| Group 1 N = 10 | 50 mg Lixivaptan in the morning, 50 mg Lixivaptan in the afternoon, for 7 days | 7-14 days | 150 mg Lixivaptan in the morning, 50 mg Lixivaptan in the afternoon, for 7 days |

TABLE 6-continued

Study Parameters

| Study Groups | Study Period 1 | Wash-out | Study Period 2 |
|---|---|---|---|
| Group 2 N = 10 | 100 mg Lixivaptan in the morning, 100 mg Lixivaptan in the afternoon, for 7 days | 7-14 days | 200 mg Lixivaptan in the morning, 100 mg Lixivaptan in the afternoon, for 7 days |
| Group 3 N = 10 | 200 mg Lixivaptan in the morning, 200 mg Lixivaptan in the afternoon, for 7 days | 7-14 days | 250 mg Lixivaptan in the morning, 150 mg Lixivaptan in the afternoon, for 7 days |
| Group 4 N = 10 | 50 mg Lixivaptan in the morning, 50 mg Lixivaptan in the afternoon, 50 mg Lixivaptan in the evening, for 7 days | 7-14 days | 100 mg Lixivaptan in the morning, 100 mg Lixivaptan in the afternoon, 100 mg Lixivaptan in the evening, for 7 days |

Patients in Groups 1-3 take study medications at 8 am and 5 pm on each study day and patients in Group 4 take study medications at 8 am, 2 pm and 8 pm on each study day. Subjects will have in-clinic assessments on days 1 and 7 of each treatment period to obtain 24-hour pharmacokinetic and pharmacodynamic data. Subjects visit the clinic from the afternoon of Day −1 through the morning of Day 2. They return at the end of each study period for a similar inpatient period (i.e., from the afternoon of Day 6 through the morning of Day 8). Except for the doses administered on Days 1 and 7 of each study period, all other doses are taken by the subject as an outpatient.

Measurements of peak maximal concentration of drug, minimum concentration, concentration at 24 hours postdose, time to maximum (peak) plasma concentration, and area under the concentration-time curve from time 0 to 24 hours postdose for lixivaptan are determined.

Example 7—Ascending Multiple-Dose, Safety, and Tolerance Study of Lixivaptan in Healthy Adult Male Subjects In a randomized, placebo-controlled, ascending multiple-dose study of lixivaptan in healthy, adult male subjects it was found that lixivaptan exerted a profound diuretic effect. After single doses of 25 mg and higher (day 1), a doubling in Uvol (0-to-4-hours) was observed. The effects on diuresis were further highlighted by the statistical comparison of the 0-to-4-hour and 0-to-24-hour urine outputs between subjects who received lixivaptan and those who received placebo. During the first 4 hours after drug administration, a single dose of 25 mg or higher resulted in significantly greater urine output than placebo. During the 0-to-24-hour collection interval, doses of 200 mg or larger resulted in significantly greater urine output than placebo across the 14 days of dose administration. The volume of urine output increased in a dose-related manner. These profound diuretic effects persisted throughout the 14 days of dose administration. Further examination of the Uvol, expressed as mL per unit time, Uflow, also revealed a dose-related increase in the duration of effects. The significant increases in Uvol on days 1 and 14, occurred during periods of fluid restriction (0-to-4-hours) and periods of fluid ad lib (>4 hours). Although there was a dose-related increase with respect to 0-to-24-hour fluid intake, no significant differences were observed with 0-to-4-hour fluid intake that would have contributed to the significantly large volumes of urine during this period.

Significant effects on decreasing $U_{osm}$ were obtained in all subjects administered lixivaptan. Across all dose groups, the minimal values of $U_{osm}$ consistently occurred within the first 2 hours after drug administration. In particular, minimal values of <300 mOsm/L were obtained with doses of 25 mg and higher. However, suppression of $U_{osm}$ were short-lived. The $U_{osm}$ values remained below this iso-osmolar point until 4 hours after a 100-mg dose and the duration for minimal values increased with dose. By day 14, the $U_{osm}$ values revealed a dose-related pattern of decreased baseline values. This is presumably due to sufficient circulating levels of lixivaptan remaining in the plasma (and at the site of action) to perpetuate the drug's action. These results mirror the action of lixivaptan on the V2 receptor, that is, decreases in the $U_{osm}$ reflected increases in solute free water excretion that continued throughout the 14 days of lixivaptan administration.

Consistent with the increases in $U_{flow}$ and decreases in $U_{osm}$, significant dose-related increases in serum osmolality were observed in all subjects given lixivaptan.

The mean time course of $U_{osm}$ obtained after various doses of lixivaptan is depicted in FIG. 3. As shown therein, doses were provided at doses of 25 mg, 50 mg, 100 mg, 200 mg, 300 mg, 400 mg, 500 mg, 600 mg, and 800 mg. Furthermore, increased doses of lixivaptan allowed for the maintenance of urine osmolality below 300 mOsm/kg for up to 12 hours (e.g., 300 mg to 800 mg doses). However, only the 800 mg dose provided suppression of $U_{osm}$ to values <300 mOsm/kg for up to 24 hours.

Furthermore, lixivaptan was found to be safe and well tolerated by healthy men at daily oral doses up to 800 mg and twice daily oral doses up to 400 mg when given for 14 consecutive days.

Example 8. Clinical Study to Establish Safety, Pharmacokinetics and Pharmacodynamics of Lixivaptan based on FDA Guidance A. Study Design. A Phase II open-label, parallel-group, multiple dose clinical study is conducted, based on FDA guidance, (1) characterizing the pharmacokinetic profile of lixivaptan following multiple doses (twice daily doses of 50 and 200 mg) in ADPKD subjects with relatively preserved kidney function (defined as chronic kidney disease (CKD) CKD1 and CKD2) and moderately impaired renal function (defined as CKD3), (2) characterizing the effect of lixivaptan on urine osmolality over a 24-hour period following multiple doses of lixivaptan in ADPKD subjects, and (3) characterizing the time course of the pharmacodynamic effect of lixivaptan on urine output, total kidney volume, liver volume, circulating vasopressin, and serum creatinine in ADPKD subjects.

The subjects are male or female, between 18 and 60 years of age (inclusive) at the time of screening, with a body mass index (BMI) between 18 and 35 kg/m² (inclusive) at the time of screening. The subjects have an estimated glomerular filtration rate (eGFR)≥60 mL/min/1.73 m² (CKD1 or CKD2), or eGFR≥30 to <60 mL/min/1.73 m² (CKD3), with eGFR calculated by the Chronic Kidney Disease Epidemiology Collaboration (CKD-EPI) equation. Subjects have been previously diagnosed with ADPKD based on modified Ravine criteria, as follows: for subjects with family history of ADPKD, a minimum of 3 cysts per kidney by sonography or 5 cysts by computerized tomography (CT) or magnetic resonance imaging (MRI); or for subjects without family history of ADPKD, a minimum of 10 cysts per kidney by any radiologic method and exclusion of other cystic kidney diseases. ADPKD subjects in the study have a confirmed CKD Classification of Stage 1, 2 or 3.

The overall study duration, including a screening period of 28 days to enroll sufficient subjects, is 66 days. The study includes two "in-clinic" periods which are used to conduct the pharmacokinetic and pharmacodynamic measurements as described below. Subjects are confined from check-in into the clinical research unit (referred to as Day-1) until Day 2 in the morning. Subjects are again confined from Day 6 in the afternoon through Day 8 in the morning.

During the outpatient days, subjects return to the clinical research unit (CRU) on Day 4 in the morning and Day 6 in the morning for a trough PK assessment. Subjects are assigned, according to their CKD classification, to take one of 2 lixivaptan oral dose regimens for 7 days as shown below. Each dose regimen includes morning (AM) and evening (PM) oral administration of lixivaptan. When subjects are confined to the CRU, the PM dose will be administered 10±0.25 hours after the AM dose. When lixivaptan is self-administered, the PM dose will be administered 10±1.0 hours after the AM dose.

| Cohort | CKD stage | Dose | N |
| --- | --- | --- | --- |
| 1 | CKD1 or CKD2 | 200 mg BID* | 8 subjects |
| 2 | CKD3 | 200 mg BID | 8 subjects |
| 3 | CKD1 or CKD2 | 50 mg BID | 8 subjects |
| 4 | CKD3 | 50 mg BID | 8 subjects |

*BID = twice a day

B. Pharmacokinetic (PK) Assessments. PK parameters are calculated based on lixivaptan concentrations: the maximum observed plasma drug concentration ($C_{max}$), the time to reach maximum plasma concentration ($t_{max}$), the area under the concentration-time curve (AUC) from time 0 until the last quantifiable concentration ($AUC_{0-t}$), AUC from time 0 until 14 hours postdose ($AUC_{0-14}$), AUC extrapolated to infinity ($AUC_{0-inf}$), the apparent terminal elimination rate constant ($\lambda z$), the terminal elimination phase half-life ($t_{1/2}$), total body clearance (CL/F), and the volume of distribution (Vz/F).

C. Pharmacodynamic (PD) Assessments. The PD analysis includes assessments of urine osmolality and urine output, total kidney volume (TKD), liver volume (LV), plasma copeptin (as a marker for circulating vasopressin) and serum creatinine. The effect of lixivaptan on urine osmolality is determined through measurements of (a) spot urine osmolality and (b) 24 h urine output during the in-clinic phase of the study. Total kidney volume (TKV) and liver volume (LV) are measured by abdominal magnetic resonance imaging (MRI) and are assessed at the beginning of the study, after completion of the scheduled treatment period, and 4 weeks after the last dose of lixivaptan. Additional PD measurements include blood urea nitrogen (BUN) and estimated glomerular filtration rate (eGFR).

Example 9. Extension Clinical Studies for Example 6 and Example 8

Subjects in extension studies first complete the clinical study described in either Example 6 or 8. Subjects are titrated to a pharmacodynamically effective dose of twice daily lixivaptan and are subsequently maintained at such a dose for up to 26 weeks. Dose escalation is conducted on a weekly basis, is guided by trough urine osmolality assessments, and is according to a prespecified titration protocol. All doses of study medication are self-administered by study participants.

The PM dose in the twice daily regimen is taken about 10 hours after the AM dose, to minimize potential nocturia associated with vasopressin antagonism. Subjects maintain adequate hydration throughout the study by adhering to a predetermined daily fluid intake regimen.

Subjects begin therapy with a 50 mg BID dose of lixivaptan. Subjects have scheduled study visits on Day 7, 14, 21 and 28 to adjust their dose of lixivaptan based on the prespecified up-titration protocol. The decision on whether to increase or adjust the dose is based on each subject's trough urine osmolality value at the time of each visit; on the subject's reported tolerability of the current dose; and on the investigator's assessment. In addition to urine osmolality, urine specific gravity is measured at each study visit listed above, as well as at the 2 Month, 4 Month, and 6 Month study visits. Serum creatinine is assessed at the Day 7 visit and at the 6 months visit.

It is claimed:

1. A method of treating autosomal dominant polycystic kidney disease (ADPKD) in a human subject, said method comprising administering to the subject a therapeutically effective amount of a pharmaceutical composition comprising lixivaptan and a pharmaceutically acceptable carrier in a divided dose regimen, wherein a total daily dose of lixivaptan is between about 200 mg and about 500 mg.

2. The method of claim 1, wherein the divided dose regimen consists of a first dose and a second dose.

3. The method of claim 2, wherein the first dose is between 125 mg and 325 mg lixivaptan.

4. The method of claim 2, wherein the second dose is between 75 mg and 175 mg lixivaptan.

5. The method of claim 2, wherein the first dose is 200 mg lixivaptan.

6. The method of claim 2, wherein the second dose is 100 mg lixivaptan.

7. The method of claim 2, wherein the second dose is administered about eight hours after the first dose.

8. The method of claim 2, wherein the second dose is administered about ten hours after the first dose.

9. The method of claim 2, wherein the second dose is administered about twelve hours after the first dose.

10. The method of claim 2, wherein the first dose is administered in the morning.

11. The method of claim 2, wherein the second dose is administered in the evening.

12. The method of claim 1, wherein the composition is administered for at least one week.

13. The method of claim 1, wherein the composition is administered for at least two weeks.

14. The method of claim 1, wherein the composition is administered for at least one month.

15. The method of claim 2, wherein the first dose is between about 75 mg and about 225 mg lixivaptan.

16. The method of claim 2, wherein the second dose is between about 75 mg and about 225 mg lixivaptan.

17. The method of claim 2, wherein the first dose is about 100 mg lixivaptan, and the second dose is about 100 mg lixivaptan.

18. The method of claim 2, wherein the first dose is about 150 mg lixivaptan, and the second dose is about 150 mg lixivaptan.

19. The method of claim 2, wherein the first dose is about 200 mg lixivaptan, and the second dose is about 200 mg lixivaptan.

* * * * *